(12) United States Patent
Chandrasekhar et al.

(10) Patent No.: US 9,632,059 B2
(45) Date of Patent: Apr. 25, 2017

(54) POTENTIOSTAT/GALVANOSTAT WITH DIGITAL INTERFACE

(71) Applicant: Ashwin-Ushas Corporation, Inc., Holmdel, NJ (US)

(72) Inventors: Prasanna Chandrasekhar, Holmdel, NJ (US); Yanjie Chai, Marlboro, NJ (US)

(73) Assignee: Ashwin-Ushas Corporation, Inc., Holmdel, NJ (US)

( * ) Notice: Subject to any disclaimer, the term of this patent is extended or adjusted under 35 U.S.C. 154(b) by 0 days.

(21) Appl. No.: 14/844,367

(22) Filed: Sep. 3, 2015

(65) Prior Publication Data

US 2017/0067848 A1    Mar. 9, 2017

(51) Int. Cl.
   *G01N 27/416*    (2006.01)
(52) U.S. Cl.
   CPC ....... *G01N 27/416* (2013.01); *G01N 27/4163* (2013.01)
(58) Field of Classification Search
   CPC ... G01R 31/02–31/026; G01R 31/2829; G01R 31/2853; G01N 27/4065;
   (Continued)

(56) References Cited

U.S. PATENT DOCUMENTS

| | | |
|---|---|---|
| 3,807,832 A | 4/1974 | Castellion |
| 3,844,636 A | 10/1974 | Maricle |

(Continued)

FOREIGN PATENT DOCUMENTS

| | | |
|---|---|---|
| CN | 101939399 A | 1/2011 |
| CN | 102176102 | 9/2011 |

(Continued)

OTHER PUBLICATIONS (Non-edited textbook): Chandrasekhar, P. Conducting Polymers: Fundamentals and Applications. A Practical Approach, with foreword by Lawrence Dalton: Kluwer Academic Publishers (now Springer Verlag), Dordrecht, The Netherlands and Norwell, MA, USAM ISBN No. 0-7923-8564-0 (Aug. 1999).

(Continued)

*Primary Examiner* — Gurpreet Kaur
(74) *Attorney, Agent, or Firm* — Morgan, Lewis & Bockius LLP

(57) ABSTRACT

A potentiostat/galvanostat employs a controller for providing digital control signals to a digital-to-analog converter (DAC) that generates an analog output signal in response to digital control signals. A high current driver produces a high current output in response to the analog output signal from the DAC. A high current monitor monitors the output from the high current driver to produce a feedback signal for the high current driver to control the current produced by the high current driver and to produce an output dependent on the current supplied from the high current driver for monitoring by the controller. A counter electrode contact for a counter electrode is connected with the output of the high current monitor. A working electrode contact for a working electrode is electrically connected with a fixed stable voltage potential to enable electrochemical analysis of material between the counter electrode and the working electrode. A low current driver produces a low current range output in response to an analog output signal from the DAC. A low current monitor monitors the working electrode contact to detect current at the working electrode contact to supply an output dependent on the current detected for monitoring by the controller and for providing a feedback signal to the low current driver in order to control the output of the low (Continued)

current driver to control current between the counter electrode contact and the working electrode contact.

10 Claims, 22 Drawing Sheets

(58) Field of Classification Search
CPC .... G01N 27/3273; G01N 27/48; G01N 27/42; G01N 27/3277; G01N 27/409; G01N 27/41; G01N 27/4062; G01N 27/417; G01N 27/419; B81B 7/008; B81B 2201/01–2201/018; F02D 41/14328; F02D 41/1496

See application file for complete search history.

(56) References Cited

U.S. PATENT DOCUMENTS

| | | | |
|---|---|---|---|
| 4,215,917 A | 8/1980 | Giglia | |
| 4,272,163 A | 6/1981 | Samokhin | |
| 4,304,465 A | 12/1981 | Diaz | |
| 4,500,840 A | 2/1985 | Galwey | |
| 4,529,873 A | 7/1985 | Ballmer | |
| 4,559,122 A | 12/1985 | Folco | |
| 4,586,792 A | 5/1986 | Yang | |
| 4,618,218 A | 10/1986 | Shaw | |
| 4,665,874 A * | 5/1987 | Kawanabe | G01N 27/4065 123/679 |
| 4,749,260 A | 6/1988 | Yang | |
| 4,874,481 A | 10/1989 | Suzuki | |
| 4,902,108 A | 2/1990 | Byker | |
| 4,939,043 A | 7/1990 | Biricik | |
| 5,079,334 A | 1/1992 | Epstein | |
| 5,095,153 A | 3/1992 | Agnes | |
| 5,124,080 A | 6/1992 | Shabrang | |
| 5,137,991 A | 8/1992 | Epstein | |
| 5,159,031 A | 10/1992 | Epstein | |
| 5,164,465 A | 11/1992 | Epstein | |
| 5,173,443 A | 12/1992 | Biricik | |
| 5,182,585 A | 1/1993 | Stoner | |
| 5,184,156 A | 2/1993 | Black | |
| 5,241,411 A | 8/1993 | Arribart | |
| 5,253,100 A | 10/1993 | Yang | |
| 5,373,305 A | 12/1994 | Lepore, Jr. | |
| 5,373,306 A | 12/1994 | Amore | |
| 5,413,739 A | 5/1995 | Coleman | |
| 5,441,629 A | 8/1995 | Kosaki | |
| 5,446,576 A | 8/1995 | Lynam | |
| 5,446,577 A | 8/1995 | Bennett | |
| 5,455,637 A | 10/1995 | Kallman | |
| 5,455,638 A | 10/1995 | Kallman | |
| 5,466,356 A | 11/1995 | Schneider | |
| 5,500,759 A | 3/1996 | Coleman | |
| 5,561,206 A | 10/1996 | Yamamoto | |
| 5,578,191 A | 11/1996 | Robert | |
| 5,608,567 A | 3/1997 | Grupp | |
| 5,657,150 A | 8/1997 | Kallman | |
| 5,728,943 A | 3/1998 | Colter, Jr. | |
| 5,835,185 A | 11/1998 | Kallman | |
| 5,864,419 A | 1/1999 | Lynam | |
| 5,900,720 A | 5/1999 | Kallman | |
| 5,951,844 A | 9/1999 | Jansen | |
| 5,969,847 A | 10/1999 | Coleman | |
| 5,973,818 A | 10/1999 | Sjursen | |
| 5,992,996 A | 11/1999 | Sawyer | |
| 5,995,273 A | 11/1999 | Chandrasekhar | |
| 6,033,592 A | 3/2000 | Chandrasekhar | |
| 6,063,253 A | 5/2000 | Shreve | |
| 6,083,376 A | 7/2000 | Akram | |
| 6,089,721 A | 7/2000 | Schierbeek | |
| 6,099,117 A | 8/2000 | Gregory | |
| 6,115,177 A | 9/2000 | Vossier | |
| 6,130,772 A | 10/2000 | Cava | |
| 6,132,583 A | 10/2000 | Stone | |
| 6,189,835 B1 | 2/2001 | Kaufman | |
| 6,261,425 B1 | 7/2001 | Huang | |
| 6,267,853 B1 | 7/2001 | Dordi | |
| 6,270,647 B1 | 8/2001 | Graham | |
| 6,279,857 B1 | 8/2001 | Roth | |
| 6,294,060 B1 | 9/2001 | Webb | |
| 6,299,751 B1 | 10/2001 | Kaufman | |
| 6,299,753 B1 | 10/2001 | Chao | |
| 6,327,069 B1 | 12/2001 | Allemand | |
| 6,339,334 B1 | 1/2002 | Park | |
| 6,402,924 B1 | 6/2002 | Martin | |
| 6,409,903 B1 | 6/2002 | Chung | |
| 6,428,684 B1 | 8/2002 | Warburton | |
| 6,538,796 B1 | 3/2003 | Swanson | |
| 6,547,945 B2 | 4/2003 | Shallow | |
| 6,551,484 B2 | 4/2003 | Hey | |
| 6,607,652 B2 | 8/2003 | Webb | |
| 6,620,304 B1 | 9/2003 | Hoffacker | |
| 6,687,631 B2 | 2/2004 | Yoon | |
| 6,713,774 B2 | 3/2004 | DeSteese | |
| 6,733,909 B2 | 5/2004 | Ding | |
| 6,818,110 B1 | 11/2004 | Warren | |
| 6,837,978 B1 | 1/2005 | Hey | |
| 6,859,297 B2 | 2/2005 | Lee | |
| RE39,043 E | 3/2006 | Nakayama | |
| 7,033,466 B2 | 4/2006 | Riewe | |
| 7,156,965 B1 | 1/2007 | Li | |
| 7,180,649 B2 | 2/2007 | Morrison | |
| 7,219,860 B2 | 5/2007 | Wehner | |
| 7,223,323 B2 | 5/2007 | Yang | |
| 7,229,545 B2 | 6/2007 | Sewing | |
| 7,247,222 B2 | 7/2007 | Yang | |
| 7,270,891 B2 | 9/2007 | Roth | |
| 7,277,215 B2 | 10/2007 | Greer | |
| 7,306,332 B2 | 12/2007 | Chen | |
| 7,333,258 B2 | 2/2008 | Yang | |
| 7,342,708 B2 | 3/2008 | Ho | |
| RE40,218 E | 4/2008 | Landau | |
| 7,355,161 B2 | 4/2008 | Romig | |
| 7,374,283 B2 | 5/2008 | Blum | |
| 7,384,522 B2 | 6/2008 | Marszal | |
| 7,390,123 B2 | 6/2008 | Friedman | |
| 7,427,338 B2 | 9/2008 | Dordi | |
| 7,427,346 B2 | 9/2008 | Tom | |
| 7,449,098 B1 | 11/2008 | Mayer | |
| 7,500,747 B2 | 3/2009 | Howell | |
| 7,578,912 B2 | 8/2009 | Buehler | |
| 7,675,667 B2 | 3/2010 | Xu | |
| 7,686,938 B2 | 3/2010 | Gill | |
| 7,691,284 B2 | 4/2010 | Cumberland | |
| 7,704,352 B2 | 4/2010 | Lopatin | |
| 7,733,335 B2 | 6/2010 | Zehner | |
| 7,738,155 B2 | 6/2010 | Agrawal | |
| 7,761,053 B2 | 7/2010 | Kruzelecky | |
| 7,828,944 B2 | 11/2010 | Nagashima | |
| 7,874,666 B2 | 1/2011 | Xu | |
| 7,940,062 B1 | 5/2011 | Miller | |
| 7,951,902 B2 | 5/2011 | Sotzing | |
| 7,952,557 B2 | 5/2011 | Amundson | |
| 7,954,942 B2 | 6/2011 | Calilung | |
| 7,999,992 B2 | 8/2011 | Mazurkiewicz | |
| 8,005,526 B2 | 8/2011 | Martin | |
| 8,016,415 B2 | 9/2011 | Figler | |
| 8,017,217 B1 | 9/2011 | Gregoire | |
| 8,018,644 B2 | 9/2011 | Gustavsson | |
| 8,109,629 B2 | 2/2012 | Howell | |
| 8,133,369 B2 | 3/2012 | Tam | |
| 8,234,507 B2 | 7/2012 | Zhu | |
| 8,241,228 B1 | 8/2012 | Cohen | |
| 8,337,014 B2 | 12/2012 | Kokonaski | |
| 8,408,699 B2 | 4/2013 | Blum | |
| 8,434,863 B2 | 5/2013 | Howell | |
| 8,465,151 B2 | 6/2013 | Howell | |
| 8,496,790 B2 | 7/2013 | Wilson | |
| 8,500,983 B2 | 8/2013 | Ponnuswamy | |
| 8,541,174 B2 | 9/2013 | Wohlstadter | |
| 8,551,315 B2 | 10/2013 | Cohen | |
| 8,603,316 B2 | 12/2013 | Cohen | |
| 8,657,438 B2 | 2/2014 | Jacobs | |
| 8,708,483 B2 | 4/2014 | Kokonaski | |

(56) References Cited

U.S. PATENT DOCUMENTS

| | | |
|---|---|---|
| 8,741,590 B2 | 6/2014 | Heller |
| 8,758,591 B2 | 6/2014 | Adeloju |
| 8,783,864 B2 | 7/2014 | Matsui |
| 8,902,486 B1 | 12/2014 | Chandrasekhar |
| 8,931,896 B2 | 1/2015 | Blum |
| 8,932,443 B2 | 1/2015 | Sto.Domingo |
| 8,944,590 B2 | 2/2015 | Blum |
| 9,018,019 B2 | 4/2015 | Parker |
| 9,018,802 B2 | 4/2015 | Sun |
| 2002/0145919 A1 | 10/2002 | Lamb et al. |
| 2002/0157959 A1 | 10/2002 | Kronenberg |
| 2002/0191270 A1 | 12/2002 | Lu |
| 2003/0202249 A1 | 10/2003 | Schierbeek |
| 2003/0214695 A1 | 11/2003 | Abramson |
| 2003/0227663 A1 | 12/2003 | Agrawal |
| 2004/0256222 A1 | 12/2004 | Griego |
| 2005/0265094 A1 | 12/2005 | Harding et al. |
| 2006/0070883 A1 | 4/2006 | Bejan |
| 2007/0008603 A1 | 1/2007 | Sotzing |
| 2007/0103761 A1 | 5/2007 | Giron |
| 2007/0215457 A1 | 9/2007 | Glassman |
| 2008/0131773 A1 | 6/2008 | Lucas |
| 2008/0245471 A1 | 10/2008 | Goad |
| 2009/0067030 A1 | 3/2009 | Liu |
| 2009/0096745 A1 | 4/2009 | Sprague |
| 2009/0114537 A1 | 5/2009 | Bourgerette |
| 2009/0118604 A1 | 5/2009 | Phan et al. |
| 2009/0203873 A1 | 8/2009 | Sotzing |
| 2009/0213282 A1 | 8/2009 | Burlingame et al. |
| 2010/0253603 A1 | 10/2010 | Righi |
| 2010/0280561 A1 | 11/2010 | Song |
| 2011/0111147 A1 | 5/2011 | Agrawal |
| 2011/0135837 A1 | 6/2011 | Burdis |
| 2011/0151317 A1 | 6/2011 | Giroud |
| 2011/0164303 A1 | 7/2011 | Hampp |
| 2011/0187684 A1 | 8/2011 | Amundson |
| 2011/0255142 A1 | 10/2011 | Ash |
| 2012/0205258 A1 | 8/2012 | Noble |
| 2012/0235900 A1 | 9/2012 | Border |
| 2013/0120821 A1 | 5/2013 | Chandrasekhar |
| 2013/0161600 A1 | 6/2013 | Sotzing |
| 2013/0235323 A1 | 9/2013 | Sotzing |
| 2013/0278989 A1 | 10/2013 | Lam |
| 2014/0097088 A1 | 4/2014 | Stowell |
| 2014/0268283 A1 | 9/2014 | Chandrasekhar |
| 2014/0284216 A1 | 9/2014 | MacNeil |
| 2015/0164371 A1 | 6/2015 | Varsavsky et al. |
| 2015/0226692 A1 | 8/2015 | Dastgheib et al. |
| 2015/0275385 A1 | 10/2015 | Chandrasekhar |

FOREIGN PATENT DOCUMENTS

| | | |
|---|---|---|
| CN | 202705536 | 1/2013 |
| CN | 203256361 | 10/2013 |
| CN | 103436946 | 12/2013 |
| CN | 103498134 | 1/2014 |
| CN | 203530467 | 4/2014 |
| EP | 0915189 | 5/1999 |
| EP | 0989209 | 3/2000 |
| EP | 1533400 | 5/2005 |
| EP | 2049943 | 4/2009 |
| WO | 9314436 | 7/1993 |
| WO | 9728484 | 8/1997 |
| WO | 9837453 | 8/1998 |
| WO | 9845504 | 10/1998 |
| WO | 0204715 | 1/2002 |
| WO | 02082172 | 10/2002 |
| WO | 2004001100 | 12/2003 |
| WO | 2005050294 | 6/2005 |
| WO | 2007146862 | 12/2007 |
| WO | 2009058877 | 5/2009 |
| WO | 2009114965 | 9/2009 |
| WO | 2012158966 | 11/2012 |
| WO | 2015014292 | 2/2015 |

OTHER PUBLICATIONS

A. Masulaitis, et al., "Use of novel dopants and doping effects for broadband signature control in conducting polymer systems," The International Society for Optical Engineering, 2528:190-197 (1995).

Chad M. Amb et al.; "Propylenedioxythiophene (ProDOT)-phenylene copolymers allow a yellow-to-transmissive electrochrome," Polymer Chemistry, (2011) 2(4): 812.

Chandrasekhar, P., et al., "High Performance Variable Emittance Devices for Spacecraft Application Based on Conducting Polymers Coupled with Ionic Liquids," AIP Conf. Proc. (2009) 1103:101-104.

Chandrasekhar, P., et al., "Large, Switchable Electrochromism in the Visible Through Far-Infrared in Conducting Polymer Devices," Adv. Funct. Mater. (2002) 12:95-103.

Chandrasekhar, P., Masulaitis, A.M.; Gumbs, R.W., "Novel Synthesis, Spectroelectrochemical, Electrochemical and Chronovoltabsorptometric Characterization of Poly(Isothianaphthene)" Synth. Met., (1990), 36(3), 303-326.

Chandrasekhar, P.; Gumbs, R.W., Novel Synthesis, Spectroelectrochemical, Electrochemical and Chronovoltabsorptometric Characterization of Family of Poly-(Aromatic Amines), Novel Processible Conducting Polymers. I. Poly(benzidines), J. Electrochem. Soc., (1991), 138, 1337-1346.

Chandrasekhar, P.; Thorne, J.R.G., Hochstrasser, R.M., Third-order Nonlinear Optical Properties of Poly(diphenyl Amine) and Poly(4-Amino Biphenyl), Novel Processible Conducting Polymers', Appl. Phys. Lett., (1991), 59, 1661-3.

Chandrasekhar, P.; Wheeler, R.A.; Hoffmann, Roald, "Sigma Bond Cleavage in Coordinated Dioxygen: The Case of the u-Peroxo Complex [(THF)3Cl2V(III)(O22)-V(III)CL2(THF)3] and Vanadyl Formation in Solution", Inorg. Chim. Acta, (1987), 129:51-59.

Extended European Search Report and Written Opinion dated Jun. 9, 2015 for European Patent Application No. 12850225.

Fillion, E.; Fishlock, D.; Wilsily, A.; Goll, J. M., "Meldrum's Acids as Acylating Agents in the Catylitic Intramolecular Friedel-Crafts Reaction," J. Org. Chem. 2005, 70, 1316.

Gazotti, W.A.; Casalbore-Miceli, G.; Geri, A.; De Paoli, M.-A., "A Solid-State Electrochromic Device Based on Two Optically Complementary Conducting Polymers", Adv. Mat. 10, 60-64 (1998).

Groenendaal, L.; Jonas, F.; Freitag, D.; Pielartzik, H.; Reynolds, J.R., "Poly(3,4-ethylenedioxythiophene) and Its Deriatives: Past, Present and Future", Adv. Mat., 12, 481-494 (2000).

Guay, J.; Dao, L.H., "Formation of poly(4-phenylaniline) by electropolymerization of 4-aminobiphenyl or diphenylamine", J. Electroanal. Chem., 274, 135-142 (1989).

Guay, J.; Leclerc, M.; Dao, L.H., "Conducting polymer derived from 4-aminobiphenyl" J. Electroanal. Chem. Interfac. Electrochem., 251, 31-39 (1988).

Hotta, S.; Rughooputh, S.D.D.V.; Heeger, A.J.; Wudl, F., "Spectroscopic Studies of Soluble Poly(3-alkylthienylenes," Macromolecules, 20, 212 (1987).

Hsu, C-Y.; Lee, K-M.; Huang, J-H.; Justin Thomas, K.R.; Lin, J.T.; Ho, K-C., "A novel photoelectrochromic device with dual application based on poly(3,4-alkylenedioxytiophene) thin film and an organic dye", Journal of Power Sources, 185, 1505-1508 (2008).

International Search Report and Written Opinion dated Mar. 29, 2013 for PCT Appln No. PCT/US2012/065123.

International Search Report dated Feb. 3, 2014 for counterpart PCT Appln. No. PCT/US2013/032320.

Ivernale, M.A.; Seshadri, V.; Mamangun, D.M.D.; Ding, Y.; Filloramo, J; and Sotzing, G.A., "Polythieno[3,4-b]thiophene as an Optically Transparent Ion-Storage Layer," Chem. Mater. 2009, 21, 3332-3336.

Krishnamoorthy, K.; Ambade, A.V.; Kanungo, M.; Contractor, A.Q.; Kumar, A., "Rational design of an electorchromic polymer with high contrast in the visible region: dibenzyl substituted poly(3,4-propylenedioxythiohene)", J. Mat. Chem. 11, 2909-2911 (2001).

Leclerc, M.; Guay, J.; Dao, L.H., "Synthesis and properties of electrochromic polymers from toluidines", J. Electroanal. Chem. Interfac. Electrochem., 251, 21-29 (1988).

(56) References Cited

OTHER PUBLICATIONS

Li, H.; Xie, K.; Yao, M.; and Xin, C., "Variable Emissivity Infrared Electrochromic Device Based on Polyaniline Conducting Polymer," Synthetic Metals (2009) 159:1386-1388.
Lu, W., et al., "Use of Ionic Liquids for Å-Conjugated Polymer Electrochemical Devices," Science (2002) 297:983-986.
Menon, R.; Yoon, C.O.; Moses, D; Heeger, A.J., "Metal-Insulator Transition in Doped Conducting Polymers", in Handbook of Conducting Polymers, 2nd Edition, p. 27, Ed by Skotheim, T.A.; Reynolds, J. (Eds.), CRC Press, Boca Rato, FL, USA, (1998).
Merve Icli-Ozkut et al.; "Substituent and heteroatom effects on the electrochromic properties of similar systems," Journal of Polymer Science Part A: Polymer Chemistry, (2011) 50(4):615-621.
Nguyen, M.T.; Dao, L.H., "Electrochemical, electrochromic, and conductive properties of poly(N-alkyldiphenylamine) polymers", J. Chem. Soc., Chem. Commun., 1221-1222 (1990).
Nguyen, M.T.; Dao, L.H., "Synthesis, characterization and properties of poly-(3-methyldiphenylamine) and poly(3-methoxydiphenylamine)", J. Electroanal. Chem. Interfac. Electrochem., 289, 37-53 (1990).
P. Chandrasekhar, et al., "Far-IR Transparency and Dynamic Infrared Signature Control with Novel Conducting Polymer Systems," The International Society for Optical Engineering, 2528:169-180 (1995).
Padilla, J; Seshadri, V.; Filloramo, J.; Mino, W.K.; Mishra, S.P.; Radmard, B.; Kumar, A.; Sotzing, G.A.; and Otero, T.F., "High contrast solid-state electrochromic devices from substituted 3,4-propylenedioxythiophenes using the dual conjugated polymer approach," Synthetic Metals 2007, 157, 261-268.
Patil, A.O.; Ikenoue, Y.; Wudl, F.; Heeger A.J., J. Am. Chem. Soc., "Water Soluble Conducting Polymers," 109, 1858 (1987).
Ram, M.K.; Maccioni, E.; Nicolini, C., "The electrochromic response of polyaniline and its copolymeric systems", Thin Solid Films, 303, 27-33 (1997).
Reeves, B.D.; Grenier, C.R.G.; Argun, A.A.; Cirpan, A.; Cunningham, G.B.; McCarley, T.D.; and Reynolds, J.R., "Synthetic Methodology Toward New Propylenedioxythiophene Polymers", Polymer Preprints 45 (1), 284 (2004).
Sapp, S.A.; Sotzing, G.A.; Reynolds, J.R., "High Contrast Ratio and Fast-Switching Dual Polymer Electrochromic Devices", Chem. Mater., 10, 2101-2108 (1998).
Schwendeman, I.; Hickman, R.; Sonmez, G.; Schottland, P.; Zong, K.; Welsh, D.M.; and Reynolds, J.R., "Enhanced Contrast Dual Polymer Electrochromic Devices", Chem. Mater., 14, 3118-3122 (2002).
Tiefenbacher, K.; Rebek, Jr., "Selective Stabilization of Self-Assembled Hydrogen-Bonded Molecular Capsules Through Å-Å Interactions," J. Am. Chem. Soc. 2012, 134, 2914.
Unur, E.; Jung, J-H.; Mortimer, R.J.; and Reynolds J.R., "Dual-Polymer Electrochromic Film Characterization Using Bipotentiostatic Control", Chem. Mater., 20, 2328-2334 (2008).
Vasilyeva, S.V.; Unur, Ece; Walczak, R.M.; Donoghue E.P.; Rinzler, A.G.; and Reynolds, J.R., "Color Purity in Polymer Electrochromic Window Devices on Indium-Tin Oxide and Single-walled Carbon Nanotube Electrodes", Applied Materials and Interfaces, vol. 1, No. 10, 2288-2297 (2009).
Welsh, D.M.; Kumar, A.; Meijer, E.W.; Reynolds, J.R., "Enhanced Contrast Ratios and Rapid Switching in Electrochromics Based on Poly(3,4-propylenedioxythiophene) Deriatives", Adv. Mat. 11, 1379-1382 (1999).
Wermuth. The Practice of Medicinal Chemistry, 1996, chapter 13, pp. 203-237.
Written Opinion of the International Searching Authority dated Feb. 3, 2014 for counterpart PCT Appln. No. PCT/US2013/032320.
Youtube Video, "Electrochromic Ballistics Protection Spectacles Prototype," http://www.youtube.com/watch?v=Wn3II82SJXg (Apr. 17, 2013).
Youtube Video, "Electrochromic Glasses Prototype," http://www.youtube.com/watch?v=yDA-Z0YauM0 (Jan. 10, 2013).
Autolab Application Note EC08, "Basic overview of the working principle of a potentiostat/galvanostat (PGSTAT)—Electrochemical cell setup," Dec. 20, 2011.
International Search Report and Written Opinion dated Jan. 30, 2015 for PCT Appln No. PCT/US2014/065170.
K. Krishnamoorthy et al. Rational design of an electrochromic polymer with high contrast in the visible region: dibenzyl substituted poly(3,4-propylenedioxythiophene). Journal Materials Chemistry, vol. 11, issue 12. Oct. 12, 2001.
Javier Padilla, Venkataramanan et al. High contrast solid state electrochromic devices from substituted 3,4-propylenedioxythiophenes using the dual conjugated polymer approach. Synthetic Metals, Issue 157, Apr. 23, 2007.
International Patent Application No. PCT/US2016/048832, Notification of Transmittal of the International Search Report and the Written Opinion of the International Searching Authority, or the Declaration, dated Dec. 30, 2016, 24 pages.

\* cited by examiner

POTENTIOSTAT/GALVANOSTAT WITH DIGITAL INTERFACE

FIELD OF THE INVENTION

The present invention relates generally to an electrochemical instrument for electrochemical analysis and more particularly to a potentiostat/galvanostat.

BACKGROUND OF THE INVENTION

Potentiostats and galvanostats are commonly used in electrochemical analysis, electrosynthesis, sensing, production and related fields. High accuracy, low cost and multiple functions (e.g., cyclic and linear scan voltammetry, various pulse voltammetric methods, AC voltammetry, electrochemical, impedance measurement, chronocoulometry, to name a few functions) are desirable properties of potentiostats/galvanostats, for research, teaching, production, sensing and other applications. It would therefore be desirable for an electrochemical instrument to have the capability to provide both potentiostat and galvanostat functions with a wide range of current as well as a practical digital interface to enable high speed performance.

SUMMARY OF THE INVENTION

In accordance with the present invention, an electrochemical instrument is provided for conducting electrochemical analysis of materials. The electrochemical instrument may be in the form of a potentiostat/galvanostat for conducting electrochemical analysis of materials positioned between a counter electrode and a working electrode of the instrument. The electrochemical instrument may comprise a controller, such as a microcontroller, for controlling operation of the circuitry of the instrument. The controller may function to operate pursuant to a computer program as well as various inputs from a user to provide various or selected parameters or modes of operation. The controller produces desired digital control signals. A digital-to-analog converter (DAC) may be provided in electrical communication with the controller for generating an analog output signal in response to digital control signals from the controller. A high current driver may be provided in electrical communication with the DAC to produce a high current range output in response to the analog output signal from the DAC. For example, the high current driver may produce a high current range output in the range of about a fraction of milliAmpere mA or a mA to about amperes As. As a specific optional example, the high current driver may produce current in the range of about 0.25 mA to about 2.5 A. A high current monitor may be provided in electrical communication with the high current driver to monitor the high current range output from the high current driver. The high current monitor may produce a feedback signal for the high current driver in response to the current monitored by the high current monitor to control the current produced by the high current driver. The high current monitor may also supply an output dependent on the current supplied from the high current driver for monitoring by the controller. The high current monitor may also supply a working output signal at a working output for performing analysis of a selected material. For this purpose, a counter electrode contact may be provided for electrical communication with the counter electrode and connectable in electrical communication with the working output of the high current monitor. A working electrode contact may be provided for electrical communication with a working electrode and may be electrically connectable with a fixed stable voltage potential (for example, ground or virtual ground) for enabling electrochemical analysis of material at or between the counter electrode and the working electrode. For example, a selected working output signal from the high current monitor may be applied from the counter electrode at or through the material being analysed or tested and then to the working electrode.

A low current driver may also optionally be provided in electrical communication with the DAC to produce a low current range output in response to the analog output signal from the DAC. For example, a low current range output may be in the range of about nanoAmperes nAs, and perhaps even as small as picoAmperes pAs, to about a mA or a fraction of a mA. As a specific optional example, the low current driver may produce current in the range of about 2.5 nA to 0.25 mA. The low current driver may be in electrical communication with the counter electrode contact so that the low current range output may be supplied by the low current driver to the counter electrode. A low current monitor may be connectable in electrical communication with the working electrode contact for detecting current at the working electrode contact. In a low current mode of operation, the low current range output from the low current driver may be supplied to the counter electrode through or at the material being analysed or tested and then to the working electrode. The low current monitor in electrical communication with the working electrode may supply an output dependent on the current detected at the working electrode contact for monitoring by the controller. The low current monitor may also provide a feedback signal for the low current driver in order to control the output of the low current driver to control the current between the counter electrode contact and the working electrode contact. The low current monitor may optionally include a monitor amplifier having an amplifier input connectable in electrical communication with the working electrode contact and having an amplifier output. The low current monitor may also include an array of feedback resistors connected between the output of the monitor amplifier and the input of the monitor amplifier. The low current monitor may also include a monitor multiplexer, for example, an analog multiplexer, in electrical communication with the controller for selecting at least one of the feedback resistors in the array for electrical communication between the output and input of the monitor amplifier to control the output of the monitor amplifier.

The high current monitor may optionally include a first high current range monitoring circuit for monitoring current in a first high current range and a second high current monitoring circuit for monitoring current in a second high current range. As an optional example, the first high current monitoring circuit may operate in a range of about mAs to about an A whereas the second high current monitoring circuit may operate in a range of about a fraction of a mA to about mAs. As a more specific optional example, the high current monitoring circuit may operate in a range of about 25 mA to 2.5 A and the second high current monitoring circuit may operate in a range of about 0.25 mA to 25 mA. Of course, the two ranges need not precisely overlap at a common end point and such common end point can be altered to a different magnitude.

The instrument may also include a reference electrode contact for electrical communication with a reference electrode for positioning relative to the working electrode and counter electrode in communication with the material, and a buffer in electrical communication with the reference electrode contact for detecting voltage at the reference electrode contact. The buffer may supply an output dependent on the voltage detected at the reference electrode contact that is buffered from the reference electrode contact for monitoring by the controller. The buffer may also selectively provide a feedback signal for the high current driver to control the output produced by the high current driver when operating in voltage mode at a high current or high power mode of operation in order to control the voltage at the reference electrode contact. The buffer may also supply the feedback signal from the buffer to the low current driver to control the output produced by the low current driver to control the voltage at the reference electrode contact when operating in voltage mode at a low current or low power mode of operation. In order to accommodate such an optional arrangement having both a high current driver and a low current driver, the instrument may also include a high current switch for switchably connecting the high current driver in and out of electrical communication with the counter electrode contact and a low current switch for switchably connecting the low current driver in and out of electrical communication with the counter electrode contact. The controller may function to enable or disable output from either or both of the high current or low current drivers to respectively provide a type of high current switch and a low current switch, respectively, to connect and disconnect from the counter electrode contact. The controller may operate to control the high current switch and the low current switch so that when the high current switch electrically connects the high current driver into electrical communication with the counter electrode contact, the controller causes the low current switch to switch the lower current driver out of electrical communication with the counter electrode contact. Likewise, when the low current switch switches the low current driver into electrical communication with the counter electrode contact, the high current switch electrically disconnects the high current driver from electrical communication with the counter electrode contact. For an optional arrangement in which the high current monitor includes both a first high current monitoring circuit and a second high current monitoring circuit, the high current switch may include a first high current monitor switch for electrically connecting the first high current range monitoring circuit in and out of electrical communication with the counter electrode contact and a second high current monitoring switch for electrically connecting the second high current monitoring circuit in and out of electrical communication with the counter electrode contact. In operation, the controller may be in electrical communication with the first and second high current monitoring switches such that when one of the high current monitoring switches is turned on the other high current monitoring switch is turned off and when at least one of the high current monitoring switches is turned on then the low current switch is turned off under the control of the controller.

The instrument may also include a ground switch under the control of the controller for electrically connecting the working electrode contact in and out of electrical communication with a fixed stable voltage potential such as ground or virtual ground. When the high current driver is switched by the high current switch to be in electrical communication with the counter electrode contact, such as when operating in a high power or high current mode of operation, the controller may control the ground switch to connect the working electrode contact to ground.

The instrument may also include a low current monitor switch under the control of the controller for switchably connecting the working electrode contact in and out of electrical communication with the low current monitor. In a low power or low current mode of operation, the low current monitor switch electrically connects the working electrode contact into electrical communication with the low current monitor and the low current switch operates to connect the low current driver in electrical communication with the counter electrode contact. In a high current or high power mode of operation, the low current monitor switch may also function to disconnect the working electrode contact out of electrical communication with the low current monitor, and the low current switch may function to disconnect the low current driver out of electrical communication with the counter electrode contact.

Next, the instrument may also include a feedback multiplexer, for example, an analog multiplexer, in electrical communication with the controller and in electrical communication with the high current monitor for receiving the feedback signal from the high current monitor, the buffer for receiving the feedback signal from the buffer, and the low current monitor for receiving the feedback signal from the low current monitor, and for switchably selecting which of the feedback signals, or a signal dependent thereon, is output by the feedback multiplexer under the control of the controller. In this regard, the controller may operate to control the feedback multiplexer to supply the feedback signal from the high current monitor for the high current driver when operating in high current mode and to supply the feedback signal from the low current monitor for the low current driver when operating in low current mode, and to supply the feedback signal from the buffer for at least one of the high current driver or low current driver when operating in voltage mode. For example, the feedback multiplexer may supply the feedback signal from the buffer for the high current driver when operating in voltage mode at a high power mode of operation and for the low current driver when operating in voltage mode at a low power mode of operation. Optionally, the first high current range monitoring circuit may provide a first high current feedback signal for the feedback multiplexer and the second high current monitoring circuit may supply a second high current feedback signal for the feedback multiplexer. When operating in the high current mode, the multiplexer under the control of the controller may selectively supply the first high current feedback signal from the first high current range monitoring circuit for the high current driver when operating in first high current range and selectively supply the second high current feedback signal from the second high current range monitoring circuit for the high current driver when operating in the second high current range. The first high current range monitoring circuit may include a first sense resistor connected in series between the high current driver and the counter electrode contact and a first differential amplifier, such as an instrumentation amplifier, connected across the first sense resistor to detect the voltage produced by the current flow through the first sense resistor to provide the first high current feedback signal. Likewise, the second high current range monitoring circuit may include a second sense resistor connected in series between the high current driver and the counter electrode and a second differential amplifier, such as an instrumentation amplifier, connected across the second sense resistor to detect the voltage produced by current flow through the second sense resistor to provide the second high current feedback signal. Preferably, the first and second sense resistors are connected in parallel circuits and have different magnitudes of resistance, optionally such as a $10^2$ magnitude difference such as 0.1 and 10 ohms for example.

The instrument may also include an analog-to-digital converter (DAC) in electrical communication with the outputs of the low current monitor, the buffer and the high current monitor to convert the output signals of the low current monitor, the buffer and the high current monitor to digital signals for the controller.

In an optional arrangement, the buffer may also be in electrical communication with the counter electrode contact for detecting a voltage at the counter electrode contact and for supplying a buffered output indicating the voltage at the counter electrode contact for electrical communication with the controller.

High Current/High Power

In accordance with the present invention an electrochemical instrument for conducting an electrochemical analysis of selected materials may be configured, adjusted or set to operate in a high power or high current mode of operation and as such may be in the configuration of potentiostat and/or galvanostat for providing selected electrical signals to a material positioned between a counter electrode and a working electrode. As configured for a high power or high current mode of operation, the electrochemical instrument may include a controller for providing digital control signals and a digital-to-analog converter (DAC) in electrical communication with the controller for generating an analog output signal in response to digital control signals from the controller. A high current driver may be in electrical communication with the DAC to produce a high current range output in response to the analog output signal from the DAC. For example, the high current range output may be in the ranges previously indicated. A high current monitor may be used in electrical communication with the high current driver to monitor the current output by the high current driver. The high current monitor may produce a current feedback signal for the high current driver in response to the current monitored by the high current monitor to control the current produced by the high current driver. The high current monitor may also supply an output dependent on the current produced by the high current driver for monitoring by the controller. The high current monitor may also supply a working output signal at a work output for application to a material, such as a material under test or analysis. For this purpose, a counter electrode contact for electrical communication with a counter electrode is connectable in electrical communication with the work output of the high current monitor. A working electrode contact for electrical communication with a working electrode may be connected in electrical communication with a fixed stable voltage potential, such as ground or virtual ground, for enabling electrochemical analysis of material at or between the counter electrode and the working electrode. The high current monitor may optionally include a first high current range monitoring circuit for monitoring current in a first high current range and a second high current monitoring circuit for monitoring current in a second high current range. For example, the first and second high current ranges may be in the ranges previously indicated. The high current monitor may also include a first high current monitor switch for electrically connecting the first high current range monitoring circuit in and out of electrical communication with the counter electrode and a second high current monitoring switch for electrically connecting the second high current monitoring circuit in and out of electrical communication with the counter electrode contact, optionally under the control of the controller which may be in electrical communication with the first and second high current monitoring switches.

The instrument may also include a reference electrode contact for electrical communication with a reference electrode for positioning relative to the working electrode and the counter electrode in communication with the material. A buffer may be provided for electrical communication with the reference electrode contact for detecting voltage at the reference electrode contact and for supplying an output dependent on the voltage at the reference electrode contact that is buffered from the reference electrode contact for monitoring by the controller. The buffer may also provide a feedback signal for the high current driver to control the output produced by the high current driver to control the voltage at the reference electrode contact.

The instrument may also include a feedback multiplexer, optionally in the form of an analog multiplexer, in electrical communication with the controller, and both in electrical communication with the high current monitor for receiving the feedback signal from the high current monitor and in electrical communication with the buffer for receiving the feedback signal from the buffer for switchably selecting under the control of the controller which of the feedback signals, or a signal dependent thereon, is output by the feedback multiplexer for the high current driver. In current mode, the controller will switch the feedback multiplexer to output the feedback signal from the high current monitor for feedback for the high current driver. In voltage mode, the controller will switch the feedback multiplexer to output the feedback signal from the buffer for feedback for the high current driver. Optionally, the first high current range monitoring circuit may provide a first high current feedback signal for the feedback multiplexer and the second high current range monitoring circuit may provide a second high current feedback signal for the feedback multiplexer. The feedback multiplexer may operate under the control of the controller to selectively supply the first high current feedback signal, or a signal dependent thereon, from the first high current range monitoring circuit for the high current driver when operating in the first high current range and to selectively supply the second high current feedback signal, or a signal dependent thereon, from the second high current range monitoring circuit for the high current driver when operating in the second high current range.

Optionally, the first high current range monitoring circuit may include a first sense resistor connected in series between the high current driver and the counter electrode contact, and a first differential amplifier, such as an instrumentation amplifier, connected across the first sense resistor to detect the voltage generated by current flow through the first sense resistor to produce the first high current feedback signals and an output for monitoring by the controller. Likewise, the second high current range monitoring circuit may optionally include a second sense resistor connected in series between the high current driver and the counter electrode contact, and a second differential amplifier, such as an instrumentation amplifier, connected across the second sense resistor to detect the voltage generated by the current flow through the second sense resistor to produce the second high current feedback signal and an output for monitoring by the controller. Preferably, the first and second sense resistors are connected in parallel circuits and have different magnitudes of resistance, optionally such as a $10^2$ magnitude difference such as 0.1 and 10 ohms for example.

The instrument may also include an analog-to-digital converter (ADC) in electrical communication with the controller and in electrical communication with the outputs of the buffer and the high current monitor to convert the output signals of the buffer and the high current monitor to a digital signal for the controller.

Optionally, the buffer may also be connectable in electrical communication with the counter electrode contact for detecting a voltage at the counter electrode contact for supplying a buffered output representing the voltage at the counter electrode contact for electrical communication with the controller.

Low Current/Low Power

In accordance with the present invention, the electromechanical instrument may be configured, adjusted, or set to operate, for example, as a potentiostat or a galvanostat in a low current or low power mode of operation. When so configured, the instrument includes a controller for providing digital control signals, and a digital-to-analog converter (DAC) in electrical communication with the controller for generating an analog output signal in response to digital control signals from the controller. A low current driver may be positioned in electrical communication with the DAC to produce a low current range output in response to the analog output signal from the DAC. For example, a low current range may be in the range previously indicated. A counter electrode contact may be provided for electrical communication with a counter electrode and for electrical communication with the output of the low current driver. A working electrode contact may also be provided in electrical communication with a working electrode for enabling electrochemical analysis of material between the counter electrode and the working electrode. In operation, current from the low current driver may be supplied to the counter electrode for application at or through the material to be analyzed or tested and then to the working electrode.

The instrument may also include a low current monitor connectable in electrical communication with the working electrode contact for detecting current at the working electrode contact and for supplying an output dependent on the current detected at the working electrode contact for monitoring by the controller. The low current monitor may also provide a feedback signal for the low current driver in order to control the output of the low current driver to control the current between the counter electrode contact and the working electrode contact. The low current monitor may optionally include a monitor amplifier, such as a current feedback amplifier or transimpedance amplifier, having an input connectable in electrical communication with the working electrode contact and providing an output. The low current monitor may also include an array of feedback resistors connected between the output of the monitor amplifier and the input of the monitor amplifier to provide a feedback loop between the output and the input of the monitor amplifier. The low current monitor may also include a monitor multiplexer, for example, an analog multiplexer, in electrical communication with the controller for selecting at least one of the feedback resistors in the array for electrical connection between the output and the input of the monitor amplifier to control the output of the monitor amplifier.

The instrument may optionally include a reference electrode contact for electrical communication with a reference electrode for positioning relative to the working electrode and the counter electrode in communication with the material. The instrument may also include a buffer for electrical communication with the reference electrode contact for detecting voltage at the reference electrode contact. The buffer may function to supply an output dependent on the voltage at the reference electrode contact that is buffered from the reference electrode contact for monitoring by the controller. The buffer may also provide a feedback signal for the low current driver to control the output produced by the low current driver to control the voltage at the reference electrode contact. In a voltage mode of operation, the voltage at the reference electrode contact may be monitored relative to voltage at the working electrode contact, which may, for example, be a virtual ground.

The instrument may also include a feedback multiplexer, for example, an analog multiplexer, in electrical communication with the controller. The feedback multiplexer may also be in electrical communication with the buffer for receiving the feedback signal from the buffer and in electrical communication with the low current monitor for receiving the feedback signal from the low current monitor for switchably selecting which of the feedback signals input to the feedback multiplexer, or a signal dependent thereon, will be output for the low current driver under the control on the controller. In this regard, the controller may function to control the feedback multiplexer to supply the feedback signal from the low current monitor for the low current driver when operating in low current mode and to selectively supply the feedback signal from the buffer for the low current driver when operating in voltage mode.

The instrument may also include an analog-to-digital converter (ADC) in electrical communication with the controller and in electrical communication with the outputs of the low current monitor and the buffer to convert the output of the low current monitor and the buffer to a digital signal for supply to the controller for monitoring by the controller.

Optionally, the buffer may also be connectable in electrical communication with the counter electrode contact for detecting a voltage at the counter electrode contact and for supplying a buffered output representing the voltage at the counter electrode contact for electrical communication with the controller.

BRIEF DESCRIPTION OF THE DRAWINGS

The foregoing summary and the following detailed description of exemplary embodiments of the present invention may be further understood when read in conjunction with the appended drawings, wherein like elements are numbered alike throughout, in which.

BRIEF DESCRIPTION OF PREFERRED EMBODIMENTS

Figure 1:
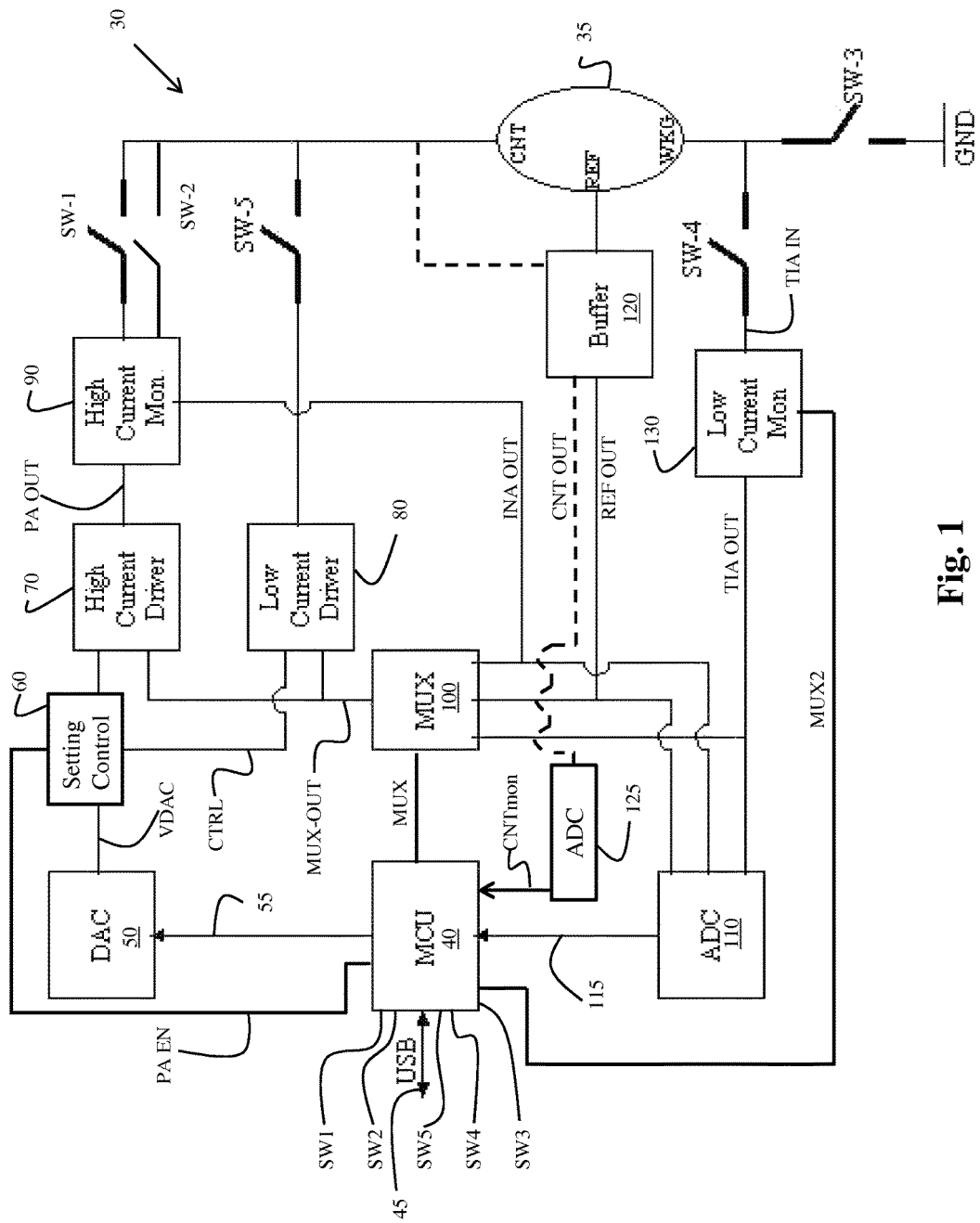
FIG. 1 schematically depicts a top-level block diagram of the potentiostat/galvanostat circuitry.

With reference to the Figs. and initially to FIG. 1, an electrochemical instrument, generally designated 30, is depicted for analyzing and testing the electrochemical properties of a material disposed or placed in the receptacle 35 intermediate a counter electrode electrically connected with counter electrode contact CNT and a working electrode electrically connected at working electrode contact WKG so that a desired electrical signal may be applied to the material through the counter and working electrode. In general, the instrument may function to apply a selected current and/or voltage signal of a desired magnitude, wave form and duration to the material within the receptacle 35 so that current flow from the counter electrode to the working electrode may be monitored. A reference electrode may be connected at a reference electrode contact REF for positioning intermediate the counter electrode and the working electrode at receptacle 35 to enable a voltage between the reference electrode and the working electrode to be monitored. In operation the electrochemical instrument may function as a potentiostat by measuring and monitoring voltages between the reference electrode contact REF and the working electrode contact WKG or as a galvanostat by measuring and monitoring currents between the counter electrode contact CNT and the working electrode contact WKG, or as a combined potentiostat/galvanostat whereby the instrument may be switched between operation as a galvanostat and a potentiostat.

In general, the instrument 30 includes a high speed controller 40, preferably provided as a microcontroller MCU, to perform all control, setting and monitoring functions of the potentiostat/galvanostat circuitry. Wide current range may be achieved, for example, from nAs (and perhaps pAs) to As, by coordination of different circuits. High speed high resolution analog-to-digital converters, ADC, 110 and digital-to-analog converters, DAC, 50 are used to achieve high accuracy and high speed. A communications interface 45, such as one or more of a UART/RS232/USB interface, such as a serial interface, e.g., RS232, USB ("Universal Serial Bus"), a parallel interface such as GPIB, and/or a wired or wireless interface such as a UART (universal asynchronous receiver/transmitter) is available to communicate with external control devices such as a computer (e.g., PC, Mac, Tablet), a network, a smart phone, or other selected device or system. Capability is also provided for a multitude of electrochemical techniques, including but not limited to, cyclic voltammetry (CV), linear scan voltammetry (LSV), various pulse voltammetric techniques (differential pulse (DPV), normal pulse (NPV), differential normal pulse (DNPV), square wave (SWV), electrochemical impedance spectroscopy (EIS) and alternating current voltammetry (ACV). New features can be added, for example by user input or software upgrading.

Figure 2:
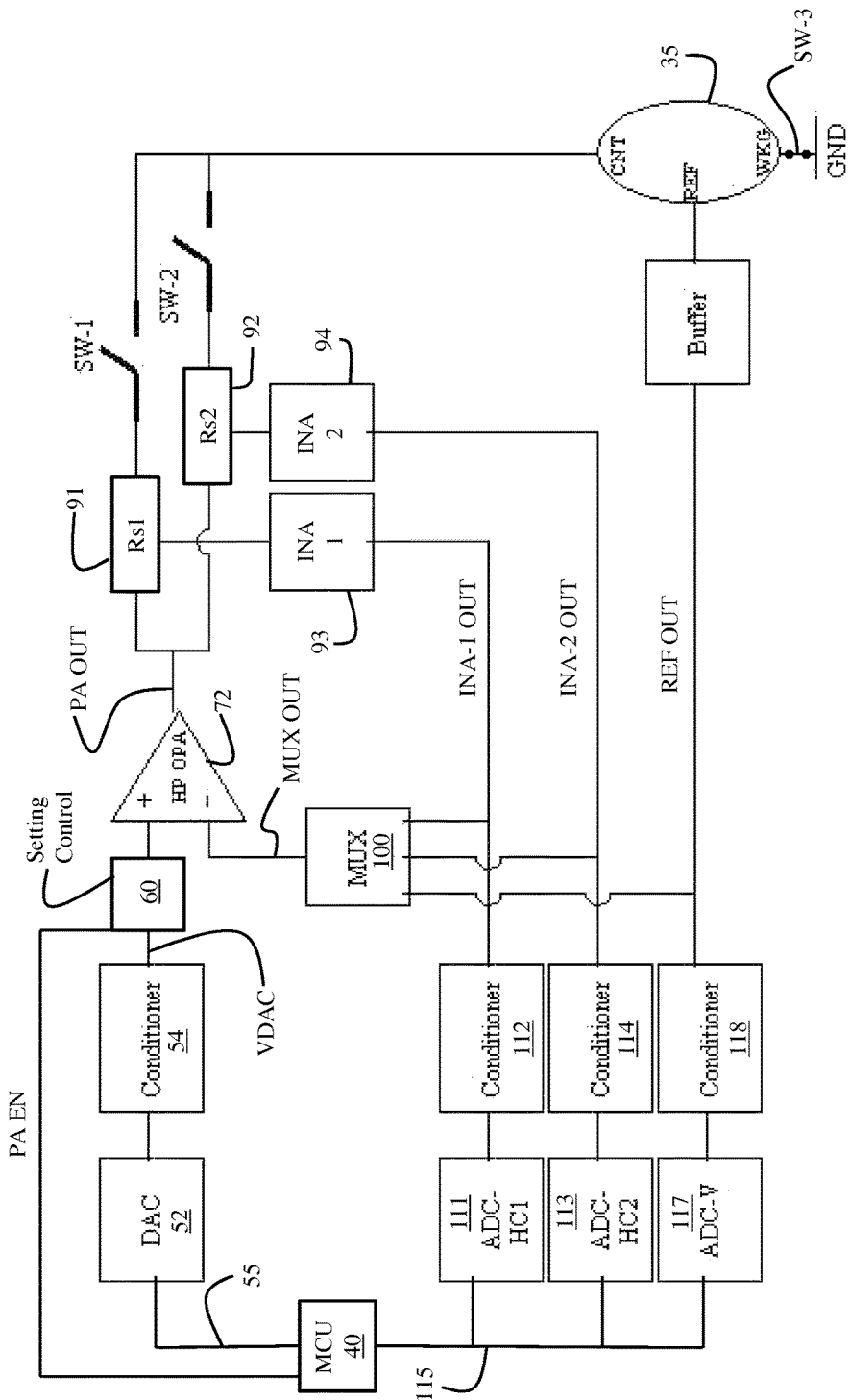
FIG. 2 schematically depicts a block diagram of a high power or high current circuit configuration for the potentiostat/galvanostat circuitry of FIG. 1.
Figure 3:
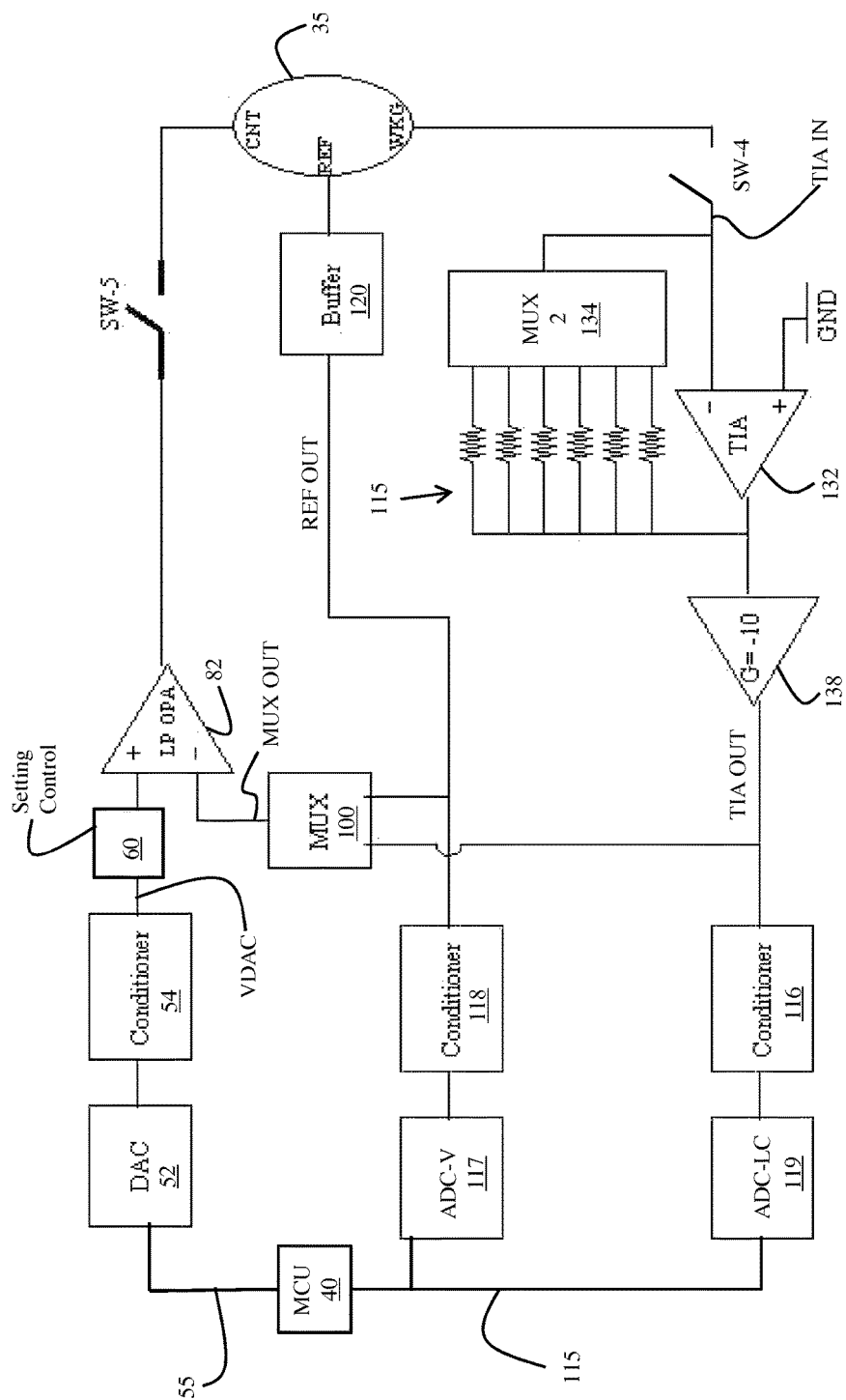
FIG. 3 schematically depicts a block diagram of a low power or low current circuit configuration for the potentiostat/galvanostat circuitry of FIG. 1.

As a general overview, referring to FIG. 1, the instrument includes a controller 40 preferably in the form of a microcontroller unit MCU that functions to execute program instructions, respond to user inputs, and monitor signals from the operational circuitry to produce digital output signals to control operation of the circuitry. Since the operational circuitry of the instrument 30 includes analog circuitry, the instrument 30 includes a DAC, preferably high resolution and high speed, responsive to digital signals from the MCU 40 to generate the required analog voltage or current to drive high current driver 70 or the low current driver 80, as shown in FIG. 1. The instrument 30 also includes a ADC, preferably high speed and high resolution, for converting selected analog signal from the analog circuitry to digital signals for the MCU 40. In a high current mode of operation, as provided by program instructions and/or user input, the DAC drives the positive input of a high power op amp HP OPA 72 as shown in FIG. 2 whereas in a low current mode of operation the DAC 50 drives the positive input of a low power op amp LP OPA 82 as shown in FIG. 3. The DAC output is controlled by the MCU and the output signal of the DAC 50 is bipolar which can be positive or negative. When a high current mode is used, the low current LP OPA output is blocked by a high isolation analog relay SW-5, and one of two high current ranges are selected by activation of one of a pair of analog relays SW-1 and SW-2 under the control of the controller 40. When a low current mode is used, the high current output is disabled by a disable pin of the high current OPA HP OPA 72 connected with the power enable line PA EN from the controller 40. The output of the respective op amp, HP OPA 72 or LP OPA 82, supplies the working output for applying a selected signal to the counter electrode contact CNT. A feedback signal dependent on the mode of operation selected (constant voltage mode or constant current mode, or high current or high power mode or low current or low power mode) is supplied to the negative input of the respective power op amp, HP OPA 72 or LP OPA 82, to form a negative feedback amplifier circuit.

An analog feedback multiplexer MUX 100 is used to select constant voltage mode or constant current mode under the control of the controller. In constant current mode, the feedback MUX 100 selects the feedback signal automatically based on the current range. In constant voltage mode, the feedback MUX 100 selects a voltage reference signal as the feedback signal. For example, the MUX 100 may function to select a constant voltage, a constant current in a high current range including, for example, a first range of high current and a second range of high current, and a constant current in a low current range.

When operating in a low current mode of operation, the low current is automatically selected by an array of precision resistors 136, as shown in FIG. 3, in a TIA circuit (a Transimpedance Amplifier Circuit) including the low current monitor circuit 130, as shown in FIG. 1, and as provided by the transimpedance amplifier TIA 132, the array of feedback resistors 136, the monitor multiplexer MUX2 134 and the negative gain amplifier 138 shown in FIG. 3. The proper resistor of the resistor array 136 is selected by MUX2 134 which is controlled by output from the MCU 40 to further select the appropriate low current.

Now, for a more detailed description of the general operation and configuration of the instrument circuitry, referring to the drawings, and initially to FIG. 1, the electrochemical instrument 30 includes a controller unit 40 in the form of a microcontroller MCU which is used to perform all desired control, setting, monitoring and communication functions for the unit. A communications interface 45 may be electrically connected with the controller MCU to enable such controller to communicate with external devices such as a computer (PC, MAC, or other type of computer device), network, smartphone or other types of external devices. The communications interface 45 may include, for example, one or more of a universal asynchronous receiver/transmitter (UART), a universal serial bus (USB) or other communication connection such as a serial RS232 or parallel GPIB. The controller MCU 40 is electrically connected with a digital-to-analog converter circuit DAC 50, preferably high speed and high resolution, via an interface bus 55 which may be in the form of a serial peripheral interface bus. The controller MCU 40 provides digital control signals for the DAC 50 which in turn generates an analog output signal on the output line VDAC in response to digital control signals from the controller, as shown in FIG. 1. The VDAC output signal from the DAC is supplied to setting control circuitry 60 which functions to selectively output a signal to a high current driver 70 and a low current driver 80. The controller 40 is also connected with the setting control circuit 60 by a power enable line PAEN which functions to enable the high current driver, when operating in high current mode, to produce the power output signal PAOUT in response to the VDAC output signal from the DAC and the power enablement signal PAEN supplied to the setting control circuit 60. When the high current driver is enabled to produce the power out signal PAOUT, switch SW-5 is opened under the control of the controller 40 to disconnect the low current driver 80. Alternatively, when the controller 40 functions to produce a low current output from the low current driver 80, when operating in low current mode, the power enablement line PAEN is not enabled to prevent the high current driver from providing an output and switch SW-5 is closed to thereby connect the low current driver 80. The setting control circuit 60 supplies a signal to the low current driver 80 over the control line CTRL to drive the low current driver to produce an output. A high current monitor 90 is connected with the output of the high current driver along the PAOUT line and functions to monitor the current produced by the high current driver at PAOUT and to produce an output signal in response to the current being monitored on the PAOUT line. Optionally, the high current monitor 90 may include separate monitoring circuits to monitor different current ranges of high current such that a first monitoring circuit for monitoring current in a first range of high current, for example, 25 mA to 2.5 A, is connected via switch SW-1 and a second monitoring circuit for monitoring current in a second range of high current, e.g., 0.25 mA to 25 mA, is connected via switch SW-2. Switch SW-1 and switch SW-2 operate under the control of the controller unit MCU 40 as shown in FIG. 1 so that a working output current is supplied from the high current monitoring circuit 90 selectively through switch SW-1 or SW-2, depending on the range of current, to the counter electrode contact CNT. The high current monitor also supplies a high current feedback signal over the INA OUT line to a feedback multiplexer MUX 100 in a form of a digitally controlled analog multiplexer 100. The high current monitor 90 also functions to supply an output signal on the INA OUT line to an analog-to-digital converter 110, preferably high speed and high resolution, which is connected with the controller 40 via interface bus 115, for example, in the form of a serial peripheral interface bus.

As shown in FIG. 1, switches SW-1 and SW-2 are connected from the output of the high current monitor 90 to the counter electrode contact CNT for connecting with a counter electrode for use at the receptacle 35. The instrument also includes a buffer circuit 120 that is connected with a reference electrode contact REF that connects with a reference electrode positioned at the receptacle 35. The reference electrode is typically positioned intermediate and spaced away from the counter electrode connected with counter electrode contact CNT and the working electrode connected with working electrode contact WKG at the receptacle 35. The reference electrode contact REF is in electrical communication with the reference electrode which is positioned relative to the working electrode and the counter electrode at the receptacle in communication with a material placed in the receptacle for analysis. The buffer electrically communicates with the reference electrode contact for detecting voltage at the reference electrode contact. The buffer functions to supply an output REF OUT that is dependent on the voltage detected at the reference electrode contact and that is buffered from the reference electrode contact for monitoring by the controller. For this purpose, the reference output line REF OUT is connected with the ADC circuit 110. In addition, the buffer provides a feedback signal at the REF OUT line to the feedback multiplexer 100 to control the output produced in a voltage mode of operation by either the high current driver 70 or the low current driver 60 depending on whether high current or power or low current or power, respectively, is being utilized. Optionally, the buffer 120 may also be separately connected with the counter electrode contact CNT to detect voltage at the counter electrode and may function to supply a buffered output signal CNT OUT to an optional analog-to-digital converter 125 that functions to convert the analog signal from the buffer on the CNT OUT line to a digital signal for supply to the controller MCU 40 to enable the controller to monitor the voltage at the counter electrode contact CNT.

As shown in FIG. 1, the working electrode contact WKG may also be connected to ground GND through switch SW-3 and connected with a low current monitor 130 through switch SW-4. When operating in high current mode, the high current monitor is connected through either switch SW-1 or switch SW-2, depending on the range of the high current, with the counter electrode contact CNT, and the working electrode contact WKG is connected to ground through switch SW-3 while switches SW-4 and SW-5 are open under the control of the controller 40. When operating in low current mode, the low current driver 80 is connected to the counter electrode contact CNT through switch SW-5 while switches SW-1 and SW-2 are open and the power enable line PA EN to the setting control circuitry 60 is disabled to disconnect the high current driver from the counter electrode contact CNT. Also in low current mode, the working electrode contact WKG is connected to the low current monitor 130 by closing of switch SW-4 while switch SW-3 is open to disconnect the working electrode contact WKG from ground under the control of the controller 40. When the working electrode contact WKG is connected via switch SW-4 to the low current monitor, a low current line TIA IN connects the low current monitor with the working electrode contact WKG. As such, the low current generated by the low current driver that passes through the material at the receptacle 35 from the counter electrode at counter electrode contact CNT to the working electrode at working electrode contact WKG is monitored by the low current monitor 130. The low current supplied from the working electrode contact WKG on the TIA IN line is monitored by the low current monitor and an output signal TIA OUT is produced reflective of the current being monitored on the TIA IN line. The TIA OUT line from the low current monitor 130 provides a feedback signal to the feedback multiplexer 100. The low current monitor also supplies an output signal that is dependent on the input current at the TIA IN to the analog-to-digital converter ADC 110 for monitoring by the controller 40 over the interface bus 115. The low current monitor is under the control of the controller by the MUX2 line that connects the controller with the low current monitor to enable the low current monitor to adjust to the current being detected at TIA IN line. The analog-to-digital converter ADC 110 functions to convert the analog signals supplied on the TIA OUT line from the low current monitor 130, the REF OUT line from the buffer 120, and the INA OUT line from the high current monitor 90 to digital signals for communication with the controller 40 over the interface bus 115. As such the instrument 30, under the control of the controller MCU, can operate in a first high current mode by opening of switches SW-2, SW-4, and SW-5, and the closing of switches SW-1, SW-3, or a second high current mode by opening of switches SW-1, SW-4, and SW-5, and the closing of switches SW-2 and SW-3, or in a voltage mode by the detection of the voltage at the reference electrode contact REF by the buffer circuit 120.

When operating in a high current mode, the controller MCU 40 can also control the feedback multiplexer 100 over the MUX line or bus so that the INA OUT signal supplied as an input to the MUX 100 is supplied at the MUX OUT line to the high current driver 70 as a feedback signal to control the output of the high current driver 70. When voltage mode is selected while the high current driver is in use the controller MCU 40 can control the feedback multiplexer 100 over the MUX line or bus to supply the REF OUT signal from the buffer 120 as a feedback signal to the high current driver 70 over the MUX OUT line to control the voltage at the reference electrode. When the instrument is operated in a low current mode, the power enablement signal from the MCU 40 causes the setting control circuit 60 to disable the high current driver 70 and switch SW-5 is closed to connect the low current driver with the counter electrode contact CNT. The controller 40 may also function to cause switches SW-1 and SW-2 to open. The controller 40 also functions to open switch SW-3 to disconnect to working electrode contact WKG from ground and to close switch SW-4 to connect the working electrode contact WKG with the low current monitor 120 which functions to monitor the low current on the TIA in line. In response to the current input on the TIA in line, the low current monitor 120 produces a feedback signal on the TIA OUT line that is supplied to the feedback multiplexer 100 that is controlled by the controller MCU to supply the TIA OUT feedback signal from the low current monitor to the low current driver 80 over the MUX OUT line when operating in low current mode. When operating in voltage mode with the low current driver in use, the controller can control the feedback multiplexer MUX 100 over the MUX OUT line or bus so that the feedback signal from the buffer over the REF OUT line is supplied by the feedback multiplexer 100 to the low current driver 80.

High Power/High Current

Referring to FIG. 2, the electrochemical instrument 30 is depicted in greater detail for configuration for use in a high power mode providing a high current mode of operation and a voltage mode of operation. As shown in FIG. 2, the controller MCU 40 functions to control the operation of the circuitry and supplies a digital control signal over interface bus 55 to a digital-to-analog converter circuit 50, as shown in FIG. 1, that includes the DAC circuit 52 connected with a conditioner circuit 54, as more specifically shown in FIG. 2. The DAC circuit 52 functions to convert the digital signals from the controller MCU 40 into analog signals that are supplied to the conditioner circuit 54 which functions to buffer and adjust the level of the signals to provide a suitable output to the setting control circuitry 60 to drive the high current driver 70 shown in FIG. 1. When operating in the high power mode, the controller 40 enables the setting control circuitry 60 over the power enable line PAEN to supply an output signal from the conditioner circuit 54 to the input of high power operational amp HP OPA 70 which may function as a high current driver. The control circuitry 60 is connected with the noninverting input or the + line of the HP OPA amp 72. The output of the HP OPA amp 72 is supplied on the power output line PA OUT, as shown in FIG. 2, as an input to the high current monitor 90 of FIG. 1 which as shown in FIG. 2 may include sense resistors RS1 and RS2, 91 and 92, respectively, and differential amplifiers INA1 93 and INA2 94. As shown in FIG. 2, the output of the high power amp HP OPA 72 is connectable with the counter electrode control CNT by a parallel circuit of the sense resistors 91 and 92. More specifically, the output of the high power amp HP OPA 72 can be switchably connected through the first sense resistor RS1 91 by switch SW-1 to the counter electrode contact CNT or alternatively through the second sense resistor RS2 92 by switch SW-2 to the counter electrode contact CNT. A first differential amplifier 93 is connected across the first sense resistor 91, which preferably is a high precision resistor, to detect the voltage generated by the current flow through the first sense resistor 91 when switch SW-1 is closed when the circuitry operates in a first range of high current. When the circuitry operates in a second range of high current, switch SW-1 is opened and SW-2 is closed so that current produced by the high power amp HP OPA 72 flows through the second sense resistor 92 to the counter electrode contact CNT. The current flow through the second sense resistor RS2 92 is detected by a second differential amplifier 94 connected across the second sense resistor 92, which preferably is a high precision resistor, to detect the voltage generated by the current flow through the second sense resistor 92. Accordingly, as shown in FIG. 2, a first high current range monitoring circuit includes the first sense resistor 91 and first differential amplifier 93 for monitoring current in a first current range of high current. Likewise, a second high current monitoring circuit includes the second sense resistor 92 and the second differential amplifier 94 first for monitoring current in a second current range of high current. The first differential amplifier 93 may be in the form of an instrumentation amplifier INA1 whereas the second differential amplifier 94 may be in the form of a second instrumentation amplifier INA2. In high current mode, the current sensing resistor (RS1 or RS2) voltage drop is thereby sampled by a high accuracy INA amplifier having a fixed gain to provide enough signal strength to provide a feedback signal. As shown in FIG. 2, the first differential amplifier 93 produces an output signal on the INA-1 OUT line connected at the output of the differential amplifier 93 for supply to conditioner circuit 112 and then to the analog-to-digital converter ADC circuit ADC-HC2 111 for electrical communication with the controller MCU 40 so that the controller can monitor the output of the first differential amplifier 93 to monitor the current flow through the first sense resistor 91 when switch SW-1 is closed. The differential amplifier 93 also supplies a feedback signal on the INA-1 OUT line to the feedback multiplexer MUX 100. Likewise, the second differential amplifier 94 provides an output signal for supply through conditioner circuit 114 and ADC circuit ADC-HC2 113 for electrical communication with the MCU 40 so that the controller can monitor the output of the second differential amplifier 94 to monitor the current flow through the second sense resistor 92 when switch SW-2 is closed. The differential amplifier 94 also supplies a feedback signal on the INA-2 OUT line to the feedback multiplexer MUX 100.

As shown in FIG. 2, the working electrode contact WKG is connected to ground GND by a closed switch SW-3 when the circuitry operates in the high power or high current mode. If the instrument 30 only operates in a high current mode, then switch SW-3 can be fixed in closed position or even be replaced by hard wire to ground a shown in FIG. 2. As also shown in FIG. 2, buffer circuitry 120 connects with the reference electrode contact REF to provide a buffered output signal on the REF OUT line to the conditioner circuit 118 and then to ADC circuit ADC-V 117 for electrical communication with the MCU 40 so that the controller 40 can monitor the reference voltage at the reference electrode contact REF. The buffer 120 functions to buffer the voltage detected at the reference electrode contact REF from the circuitry connected with the output REF OUT line of the buffer. The REF OUT line of the buffer also supplies a feedback signal from the buffer to the feedback multiplexer MUX 100.

Under the control of the MCU 40 the feedback multiplexer 100, when operating in the high current or high power mode, selects which feedback signal from the INA-1 OUT line, the INA-2 OUT line or the REF OUT line is switchably supplied as a negative feedback signal on the MUX OUT line as a negative feedback signal to the inverting terminal (the—terminal) of the high power amp HP OPA 70. When operating in the first range of high current such that switch SW-1 is closed and SW-2 is open, a first range of high current passing through the first sense resistor RS1 91 to the counter electrode contact CNT is detected by the first differential amplifier 93, and the MUX 100 is switched under the control of the MCU 40 to supply the INA-1 OUT line signal reflective of the current flow through the first sense resistor RS1 91 at the MUX OUT line as a negative feedback signal at the inverting terminal of the high power amp HP OPA 72. When operating in voltage mode, at the first range of high current when switch SW-1 is closed, the buffer 120 supplies a reference contact voltage signal reflective of the voltage at the reference electrode contact REF as a feedback signal to the MUX 100 so that the controller MCU 40 can control the MUX 100 to switchably supply the REF OUT signal from the buffer 120 as a negative feedback signal at the inverting terminal of the high power amp HP OPA 72. When operating in the second range of high current, switch SW-1 is open and switch SW-2 is closed under the control of the controller 40. As a result, a second range of high current passing through the second sense resistor RS2 92 to the counter electrode contact CNT is detected by the second differential amplifier 94 which provides an output reflective of the current flow through the second sense resistor RS2 92 on the INA-2 OUT line that is supplied to the MUX 100 as a feedback signal that can be switchably supplied as a negative feedback on the MUX OUT line to the inverting terminal of the high power amp HP OPA 72. When operating in voltage mode in the second range of high current, the feedback signal supplied from the buffer 120 at the REF OUT line to the MUX 100 can be switched at the MUX 100 under the control of the controller to be supplied as the negative output feedback signal to the inverting terminal of the high power amplifier HP OPA 72.

The output signal from the first differential amplifier 93 at the INA-1 OUT line is also supplied to conditioner circuit 112 that functions to condition the signal received at the INA-1 OUT line to an appropriate level for supply to the ADC circuit ADC-HC1 111 and may also function to buffer the signal received on the INA-1 OUT line from the output to the ADC converter circuit 111. The ADC circuit 111 functions to convert the analog signals supplied from the conditioner circuitry 112 to a digital signal for the controller 40. Likewise, the output of the second differential amplifier 94 is connected to a conditioner circuit 114 over the INA-2 OUT line which functions to condition the analog signal to an appropriate level to supply to the ADC circuit 113 ADC-HC2 113 and may also function to buffer the signal supplied on the INA-2 OUT line from the signal supplied to the ADC circuit 113. The ADC circuit 113 functions to convert the analog signals from the conditioner circuitry 114 to a digital signal for the controller 40. The output of the buffer supplied on the REF OUT line is also supplied to a conditioner circuit 118 that functions to adjust the level of the analog signal supplied on the REF OUT line for supply to the ADC circuit ADC-V 17 which functions to convert the analog signal supplied to the ADC-V 117 to the appropriate digital signal for supply to the controller MCU 40. The conditioner circuit 118 may also function to buffer the input supplied on the REF OUT line from the output to the ADC circuit ADC-V 117. The analog-to-digital converters, ADC-HC1 111, ADC-HC2 113, and ADC-V 117, are preferably high-speed and high accuracy converters that communicate with the MCU 40 over interface bus 115. As such, the MCU 40 may function to monitor the current flow through the first sense resistor 91 via the output of ADC-HC1 111, the current flow through the second sense resistor 92 via the output of ADC-HC2 113, and the voltage at the voltage reference contact REF via the output of ADC-V 117.

Low Power/Low Current

Referring to FIG. 3, the electrochemical instrument 30 is depicted with circuitry configured for use in a low power mode of operation providing a low current mode of operation and a voltage mode operation. As shown in FIG. 3, the controller MCU 40 provides digital control signals over interface bus 55 to the DAC circuit 50 as shown in FIG. 1 which includes the digital-to-analog converter circuit DAC 52 and associated conditioner circuit 54, as shown in FIG. 3. The DAC circuit 52 functions to convert the digital signal from the controller 40 to a suitable analog signal that is supplied to conditioner circuit 54. The conditioner circuit 54 functions to adjust the level of the analog output from the DAC 52, and to buffer the output of DAC 52, to a suitable level for supply to the setting control circuitry 60 which in turn supplies an output to the noninverting pin of a low power op amp LP OPA 82. The low power op amp circuit LP OPA 82 may function as a low current driver 80, as shown in FIG. 1. The output of the low power op amp LP OPA 82 is connected through switch SW-5 to the counter electrode contact CNT. When operating in low current mode, switch SW-4 is closed to connect the working electrode contact WKG with the input of the low current monitoring circuitry 130 as shown in FIG. 1. If the instrument 30 only operates in low power or low current mode switches SW-5 and SW-4 may remain closed or may replaced with a hard wire connection. As shown in FIG. 3, the working electrode contact WKG is connected through switch SW-4, which is closed when operating in low current mode, so that the current flow from the working electrode contact WKG is supplied to the inverting input of an amplifier 132 such as a current follower or transimpedance amplifier TIA in form of an op amp TIA 132 having its noninverting terminal connected to ground GND. The output of the transimpedance amplifier TIA 132 is connected through an array of feedback resistors 136 to a monitor multiplexer MUX2 134, in the form of an analog multiplexer, that operates under the control of MCU 40, that is in turn connected back to the inverting input of the transimpedance amplifier TIA 132 to provide a feedback signal loop for the amplifier TIA 132. The monitor multiplexer 134 operates under the control of the controller to select the appropriate resistor in the resistor array 136 having the appropriate resistance for the current being monitored in the low current mode of operation for connection in the feedback loop.

The output of amp TIA 132 is supplied through a negative gain amplifier 138 having a gain of negative 10, for example, to invert the output of the transimpedance amplifier TIA 132 and to amplify such signal to a suitable level for monitoring by MCU 40. The low current monitoring circuit 130 shown in FIG. 1 includes the amp TIA 132, the negative gain amplifier 138, the monitor multiplexer MUX2 134, and the feedback array of resistors 136 shown in FIG. 3. The negative gain amplifier 138 creates sufficient gain so that an output signal from the negative gain amplifier 138 is supplied at the PIA OUT line through a conditioner circuit 116 to an ADC circuit 119 for communication over the interface bus 115 to the controller so that the controller can monitor the amount of current being detected and monitored at the TIA IN line. The conditioner circuit 116 functions to condition the analog signal on the TIA OUT line to an appropriate level and to buffer such signal for supply to the analog-to-digital converter ADC-LC 119 that functions to convert the analog signal supplied by the conditioner circuit 116 to an appropriate digital signal for supply over the interface bus 115 to the controller 40. The output signal from the amplifier 138 at the TIA OUT line is also supplied as a feedback signal to the feedback multiplexer MUX 100.

As shown in FIG. 3, the buffer circuit 120 electrically connects with the reference electrode contact REF to supply a buffered output signal at the REF OUT line reflective of the voltage detected at the reference electrode contact REF. In this regard, the buffer 120 supplies a buffered feedback signal reflective of the voltage detected at the reference electrode contact REF as in input to the feedback multiplexer MUX 100 on the REF OUT line. The buffer 120 also supplies an output signal on the REF OUT line reflective of the voltage detected at the reference electrode contact REF for supply to the MCU 40 through conditioner circuit 118 and then through an ADC circuit ADC-V 117. The conditioner circuit 118 functions to condition and buffer the analog signal supplied from the REF OUT line to the appropriate level for the ADC converter ADC-V so that the converter ADC-V functions to convert the analog signal from the conditioner 118 to an appropriate digital output for supply to the controller 40 over bus 115 so that the level of voltage at the reference electrode contact REF can be monitored by the controller. The feedback multiplexer MUX 100 operates under the control of the controller so that the feedback signal on the TIA OUT line can be switchably supplied as a negative feedback at the inverting terminal of the low power amplifier LO OPA 82 when operating in low current mode. When operating in voltage mode, the controller MCU 40 can control the feedback multiplexer MUX 100 to separately supply the feedback signal at the REF OUT line from the buffer 120 reflective of the voltage detected at the reference electrode contact REF as a negative feedback signal to the inverting terminal of the low power amp LP OPA 82. In operation, the MCU 40 may function to monitor the current flow from the working electrode contact WKG via the output of ADC-LC 119 and the voltage at the reference electrode contact REF via the output of ADC-V 117, with ADC-V 117 and ADC-LC 119 preferably being high-speed and high-accuracy converters that communicate with the controller MCU 40 over interface bus 115.

Circuitry Components

Figure 4:
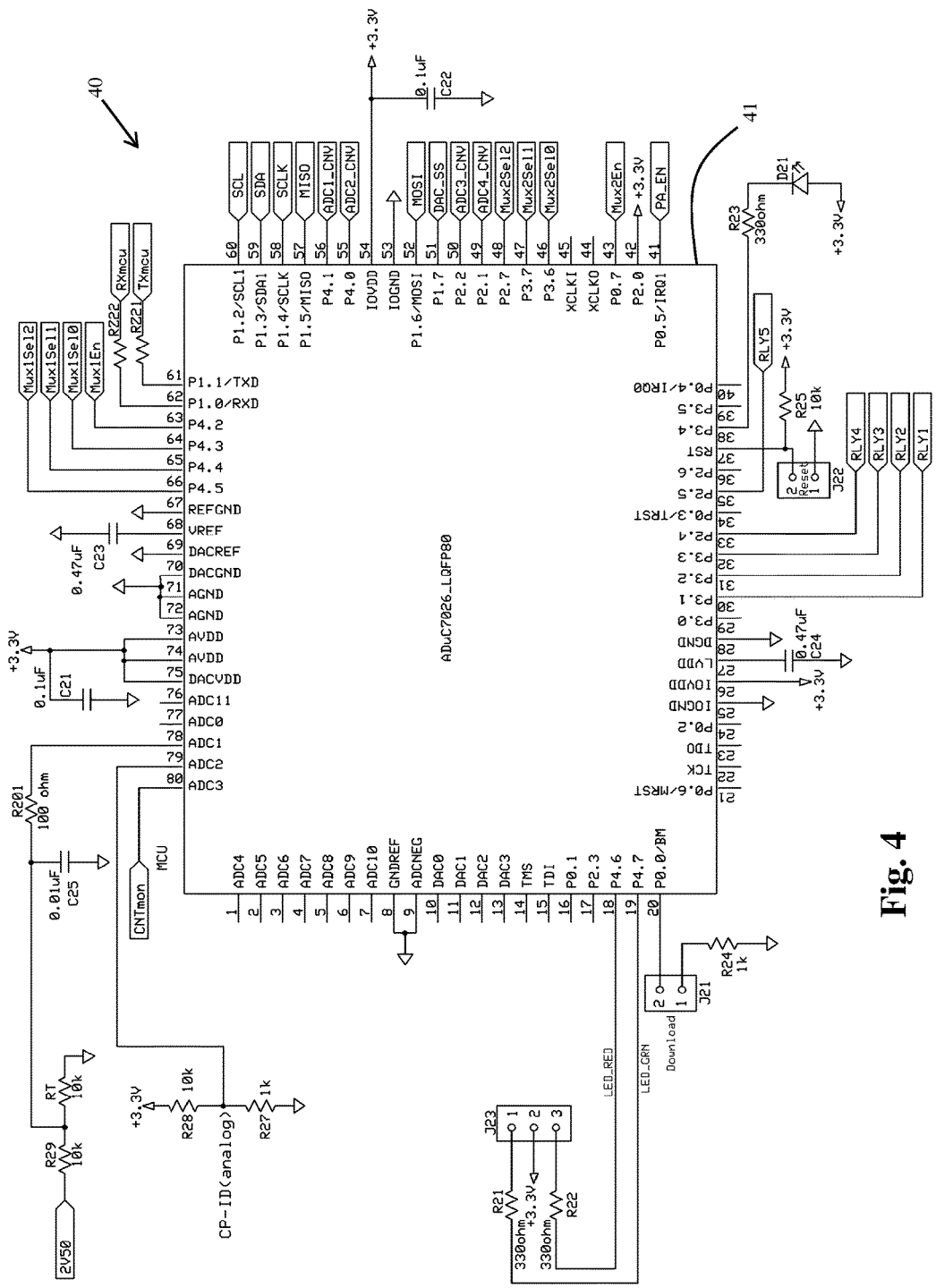
FIG. 4 is a circuit diagram of a microcontroller circuit used in the potentiostat/galvanostat circuit of FIGS. 1-3 as shown in general by the MCU in FIGS. 1-3.

Now, considering the operation of the circuitry in greater detail, the controller 40, with reference to FIG. 4, includes a microcontroller circuit 41 in the form of controller chip ADuC7026_LQFP80. The microcontroller chip 41 functions to execute computer programs, receive user inputs, and monitor and control the operation of the circuitry for the electrochemical instrument 30. As depicted in FIG. 4, the microcontroller chip 41 has several of its pins connected directly or indirectly to a voltage source of approximately 3.3 volts. For example, pin 38 is connected to a 3.3 volt source through LED D21 that illuminates to reflect operation of the instrument 30.

Figure 20:
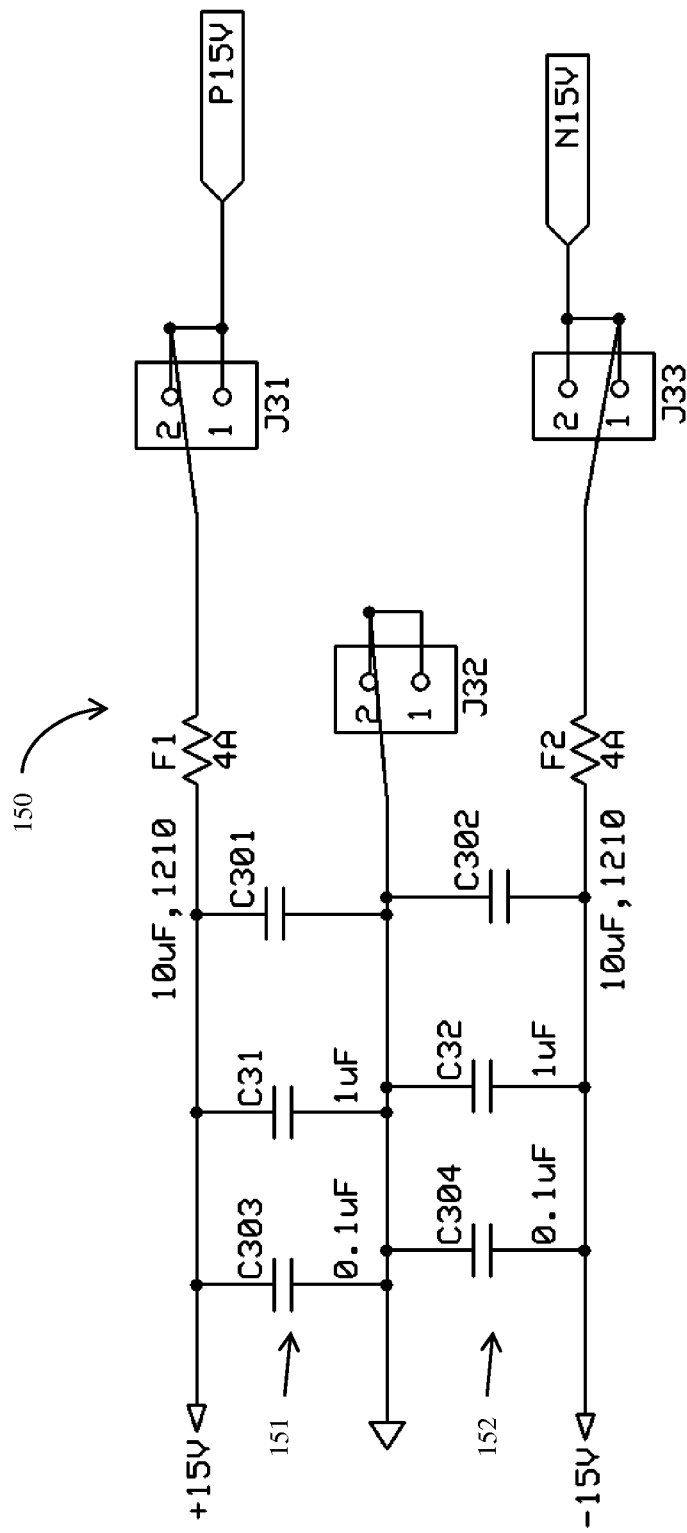
FIG. 20 is a circuit diagram of a voltage filter circuit to provide a filtered supply voltage of +15 volts and −15 volts for the circuitry as shown in FIGS. 4-23.
Figure 21:
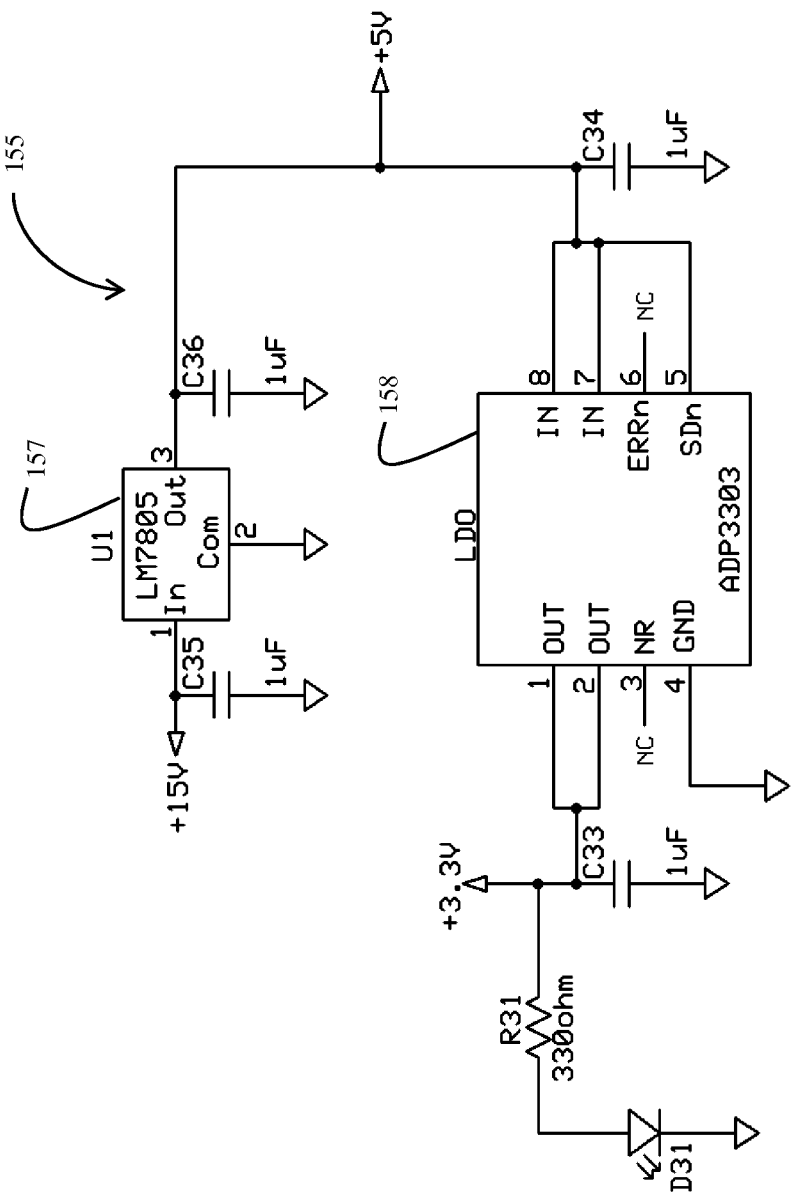
FIG. 21 is a circuit diagram of power supply circuitry for providing outputs of 5 volts and 3.3 volts for the circuitry as shown in FIGS. 4-23.

For purposes of generating proper supply voltage for the circuitry, a filter circuit, as shown in FIG. 20, is connected at jack J31 to a positive 15 volt source P15V and to a negative 15 volt source N15V at jack J33 each across a respective array of capacitors 151 and 152, that are also connected to ground at jack J32 so that a filtered output voltage of +15 volts and −15 volts is generated as well as a ground connection. The output of +15 volts is connected with an input of a power supply circuit 155 as shown in FIG. 21. As depicted a +15 volt source is supplied to the input of a voltage regulator U1 157 provided as regulator chip LM7805, such that a 5 volt output is produced at the output of the regulator U1. The output of the voltage regulator U1 is also supplied as an input to a low drop out regulator circuit LDO 158, provided by chip ADP3303, such that a +3.3V output is produced at the output of the low drop out regulator chip LDO 158 as shown in FIG. 21. The 3.3 volt output from the low drop out regulator chip LDO may be supplied to circuit components as necessary including the microcontroller chip 41 as shown in FIG. 4.

Figure 17:
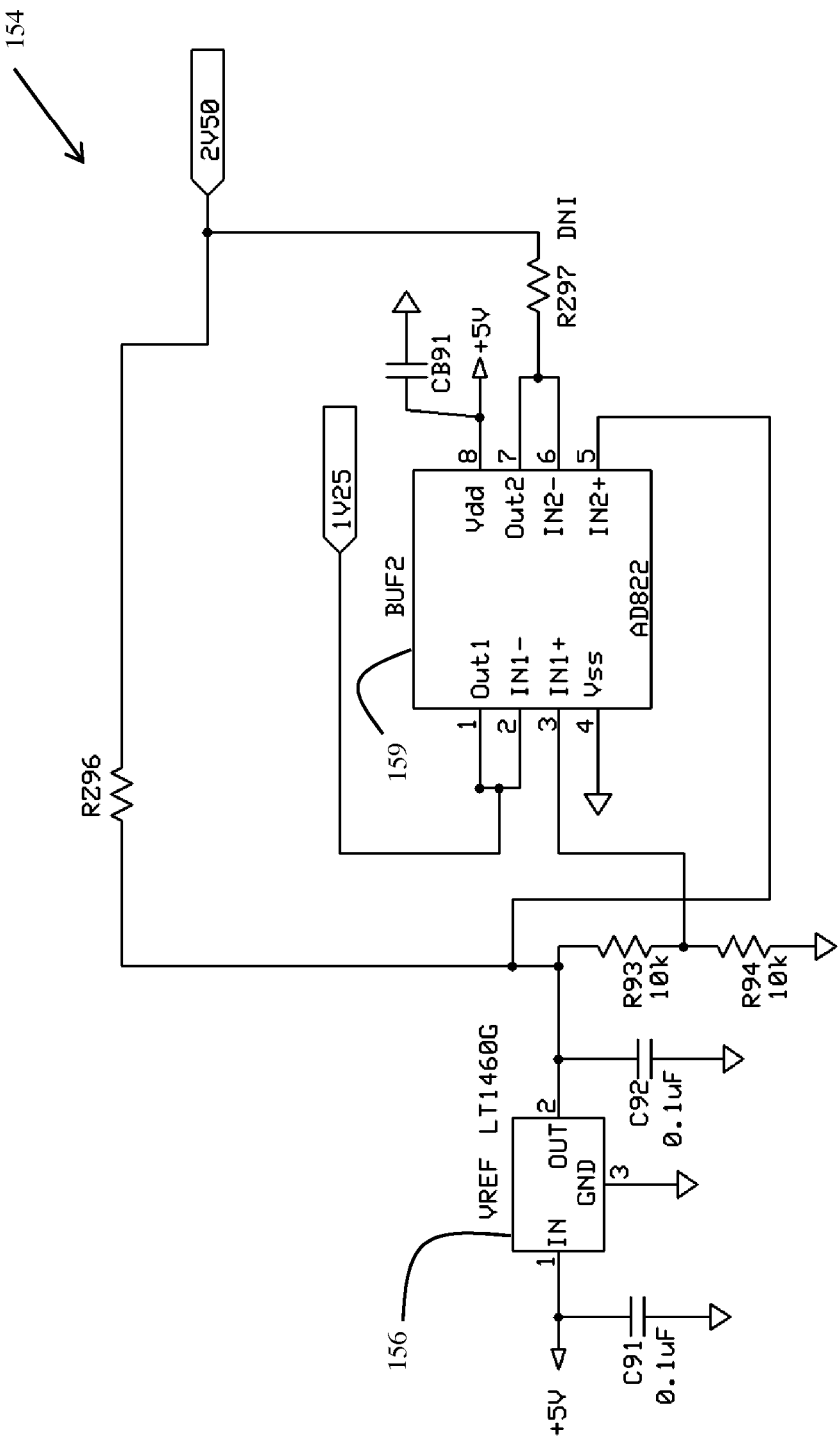
FIG. 17 is a circuit diagram of a reference voltage circuit for generating reference voltages of 1.25 volts 1V25 and 2.5 volts 2V50 for the circuitry as shown in FIGS. 4-23.

The microcontroller chip 41, as shown in FIG. 4, is also connected with a voltage reference of +2.5V at 2V50 at pin 78 as shown in FIG. 4. In order to produce selected voltage references, a voltage reference circuit 154 is provided as shown in FIG. 17. As shown, a voltage reference chip VREF 156, as provided by chip LT460G, is connected with the 5 volt input source from the power supply circuitry 155. The voltage reference chip VREF 156 is connected with a buffer BUFF 2 159, provided by chip AD822, to provide a first buffered voltage reference of 2.5 volts 2V50 and a second buffered reference voltage of 1.25 volts 1V25. The 2.5 volt reference 2V50 is connected with the microcontroller 41 at pin 78 as shown in FIG. 4.

As shown in FIG. 4, pins 18 and 19 of the microcontroller 41 are connected with Jack J23 that can be used to illuminate a red and green LED respectively. Pin 20 of the microcontroller 41 is connected with a download Jack J21 that can be used to connect with a medium or device to download information, instructions or programming, such as program updates.

Figure 18:
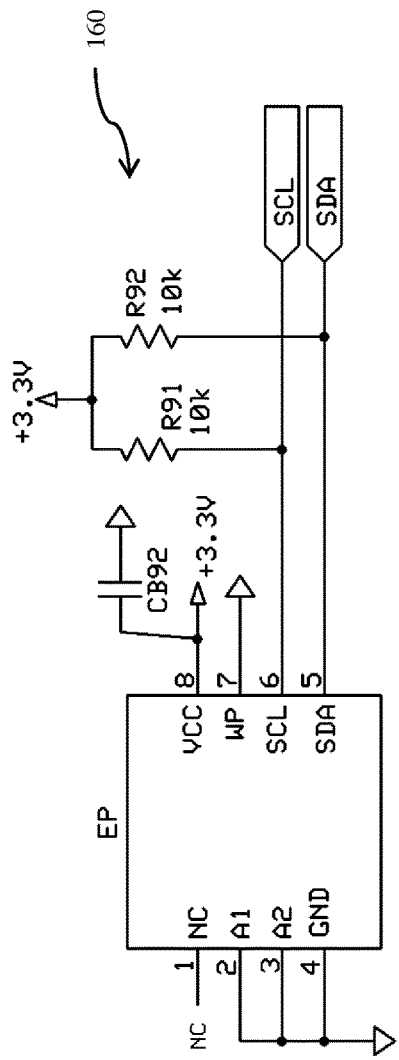
FIG. 18 is a circuit diagram of an erasable programmable memory chip EP (EPROM) and associated circuitry for providing memory and program memory for the controller MCU as shown in FIGS. 1-4.

Referring to FIG. 18, computer memory 160 is provided in the form of an EEPROM (electrically erasable and programmable read only memory) chip EP and associated circuitry for storing selected programming instructions and parameters for use by the microcontroller 41 shown in FIG. 4. The foregoing instructions and parameters may be changed by reprogramming the memory. The EP chip communicates with the microcontroller 41 over line SCL which provides a clock line to pin 60 of the controller and line SDA which provides a data line, such as a serial data line, to pin 59 of the microcontroller as shown in FIG. 4.

Figure 19:
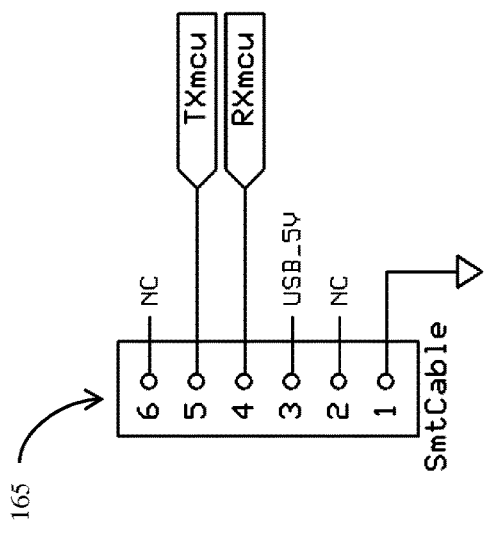
FIG. 19 is a circuit diagram of a communications port for the controller MCU as shown in FIGS. 1-4.

The microcontroller 41, as shown in FIG. 4, also includes a reset circuit connected at pin 37 and Jack J22 to enable a reset of the microcontroller 41. The microcontroller 41 also includes a communications port, at pins 61 and 62 for example, to enable the chip to communicate with external devices such as computers, networks, smartphones and/or other selected media. For this purpose the microcontroller 41 includes a port for connection with a transmission line at TXmcu and a reception line at RXmcu connected respectively at pins 61 and 62 which in turn may connect with a communications jack 165 such as a smart cable jack as shown in FIG. 19.

Figure 22:
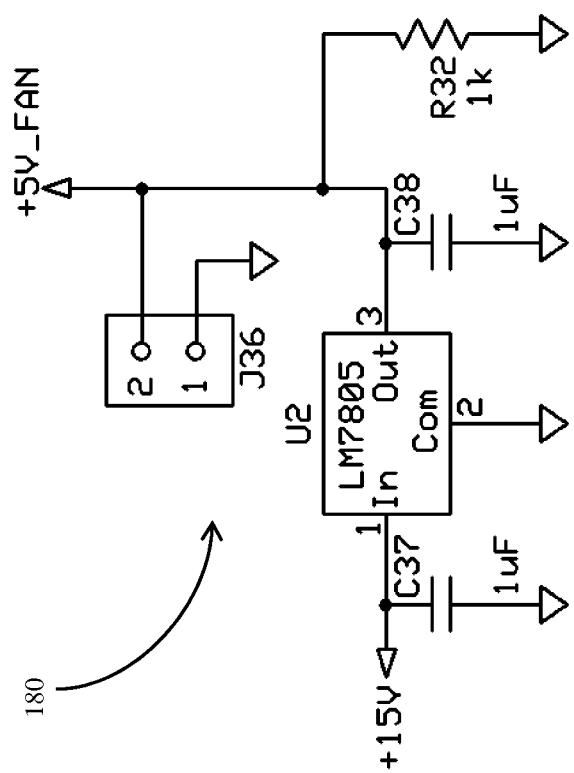
FIG. 22 is a circuit diagram of fan circuitry for operating a fan for cooling the instrument having the circuitry generally shown in FIGS. 1-23.

In order to remove heat from the instrument, the instrument 30 also includes fan circuitry 180 to drive a fan as shown in FIG. 22. Briefly, a 15 volt input is supplied at a voltage regulator circuit U2, provided by chip LM7805, which is in turn supplies a 5V output to a jack J36 which connects with the fan.

Figure 5:
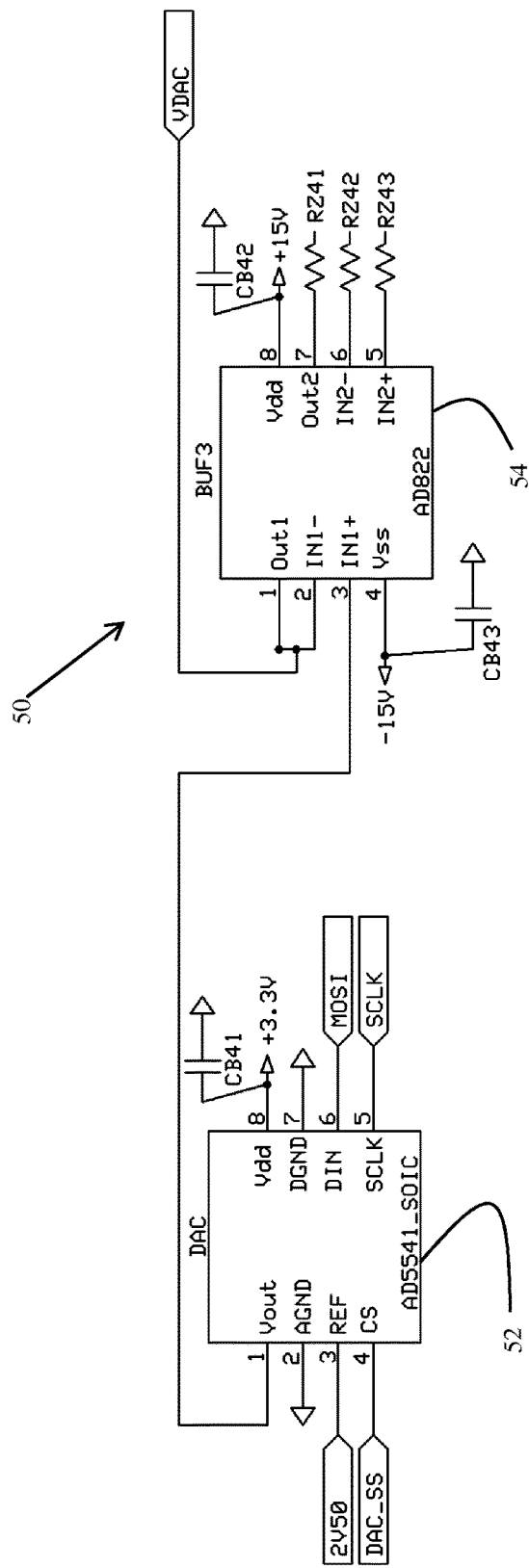
FIG. 5 is a circuit diagram of digital-to-analog circuitry (DAC) employing a DAC circuit and a conditioner circuit for the potentiostat/galvanostat circuit as shown in general by the DAC in FIGS. 1-3.

The microcontroller 41 of FIG. 4 also communicates with a digital-to-analog converter DAC 50, as shown in FIG. 5, over interface bus 55 as shown in FIG. 1. As more specifically shown in FIGS. 4 and 5, the microcontroller 41 communicates with the digital-to-analog circuit DAC 50 by an interface bus 55 that includes a master output/slave input line MOSI connected between pin 52 of the microcontroller 41 and pin 6 of a digital-to-analog converter chip DAC 52, as provided by chip AD5541_SOIC, as shown in FIG. 5, and by a slave-select line DAC_SS connected between pin 51 of the microcontroller 41 and pin 4 of the DAC chip, and by a serial clock line SCLK connected between pin 58 of the microcontroller 41 and pin 5 of the DAC chip 52. As shown in FIG. 5, the DAC chip 52 is also connected to a reference voltage a 2.5 volt reference voltage 2V50 at pin 3. The microcontroller 41 provides digital signals to the DAC chip DAC 52 over the MOSI line and selects the DAC chip 52 for operation over the slave-select line DAC_SS. Timing clock signals are supplied over the clock line SCLK. As shown in FIGS. 2 and 3, the DAC chip 52 in response to digital signals from the microcontroller provides an analog output signal to input pin 3 of a buffer circuit BUFF3 54, provided by chip AD 822, which functions as conditioner circuitry 54 as shown in FIGS. 2 and 3 to provide a buffered and conditioned analog output signal VDAC at the output pin 1 of the buffer chip BUFF3 54 as shown in FIG. 5 at a suitable level for driving a current or power driver.

Figure 7:
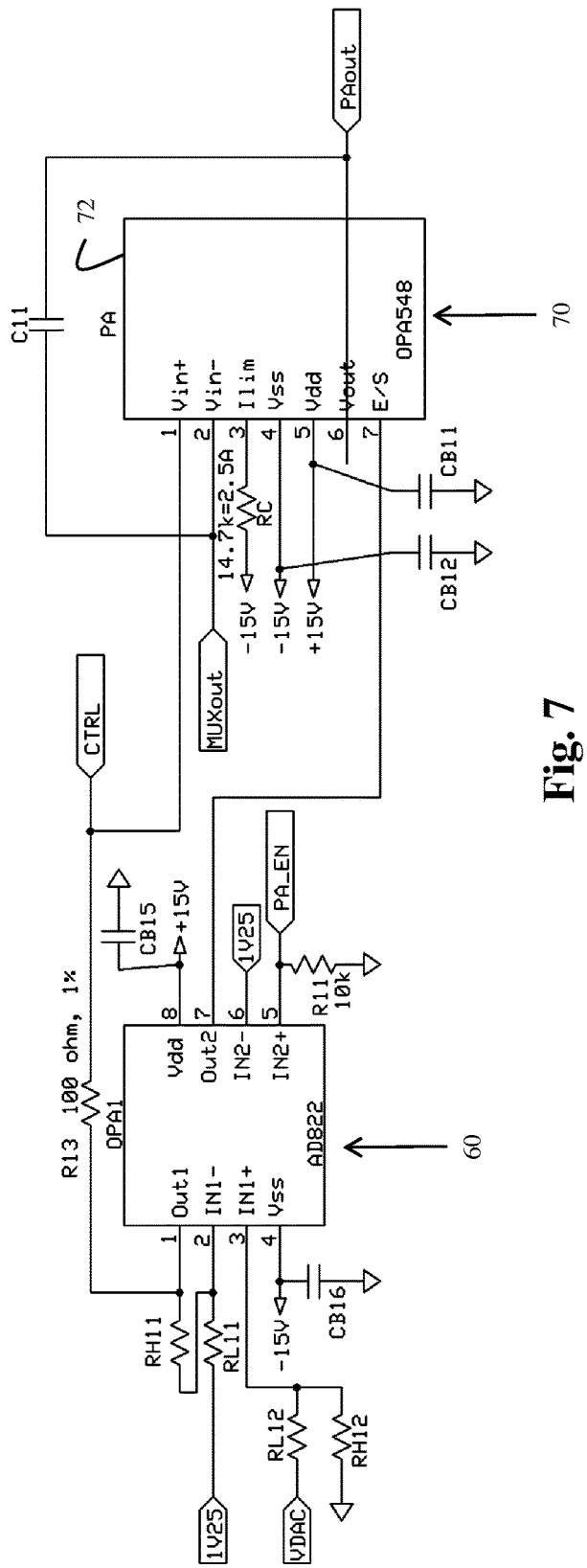
FIG. 7 is a circuit diagram of the setting control circuit shown in general in FIGS. 1-3 and the high current driver shown in FIG. 1 and as more specifically depicted as a high power op amp HP OPA in FIG. 2.

The output VDAC from the conditioner circuit 54 is supplied as an input to the setting control circuitry 60 as shown in FIG. 7. More specifically, the output VDAC from the conditioner circuitry 54 is supplied as an input at pin 3 of an op amp OPA1, as provided by chip AD822 and associated circuitry, as shown in FIG. 7, which functions as the setting control circuitry 60 shown in FIGS. 1-3. The microcontroller 41 is also in electrical communication with op the amp OPA1, as shown in FIG. 7, over power enable line PA_EN that functions to enable the high power op amp HP OPA 72 (shown in FIG. 2), which may function as a high current driver 70 (as shown in FIG. 1). The high power op amp HP OPA 72, shown in FIG. 2, includes the power amp chip PA, specifically provided as chip OPA548 and associated circuitry shown in FIG. 7, to provide a high power output on the output line PAout when the setting control circuit 60 produces an output control signal at the CTRL line from pin 1 of OPA1 that is supplied to pin 1 of the PA 72 of the high power op amp HP OPA 72, as shown in FIGS. 2 and 7, and when the controller provides an enablement signal on the PA_EN line to the setting control circuit 60 as shown in FIG. 7. As shown in FIGS. 4 and 7, the power enablement line PA_EN connects between pin 41 of the controller 41 as shown in FIG. 4 and with pin 5 of setting control circuit OPA1 60 as shown in FIG. 7. In order to disable output from the high power amp 70, the controller disables the power enablement line PA_EN to thereby disable the output PAout from the high power amp 72. As shown in FIG. 7, the setting control circuit 60 also produces an output control signal at the CTRL line from pin 1 of OPA1 that is supplied to a low power op amp circuit 82 (shown in FIG. 3) which functions as a low current driver 80 (shown in FIG. 1) as depicted in FIGS. 3 and 9.

Figure 9:
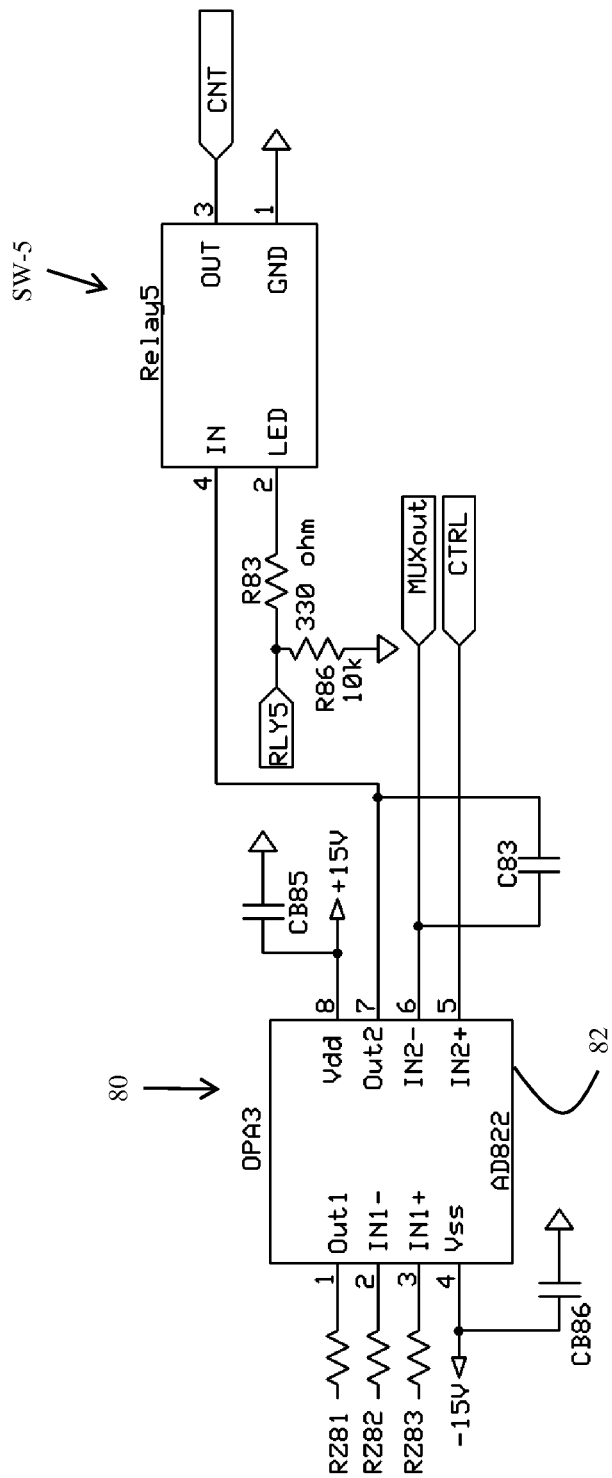
FIG. 9 is a circuit diagram of the low current driver and associated switch SW-5 as shown in FIG. 1 and as shown in more detail by the low power op amp LP OPA and switch SW-5 in FIG. 3.

The low current driver 80 (shown in FIG. 1) includes a low power op amp LP OP 82 (shown in FIG. 3) in the form of an op amp OPA3 as provided by chip AD822 and the associated circuitry as shown in FIG. 9. Now, with reference to FIG. 9, the control signal CTRL from the setting control circuit 60 is supplied as an input at pin 5 of op amp OPA3 82. The output of op amp OPA3 82 at pin 7 is supplied as an input to a switch SW-5 that is provided by a digitally controlled analog relay RELAY5 as shown in FIG. 9. The microcontroller 41 communicates with the relay RELAY5, that operates as switch SW-5, over the relay line RLY5 that is connected between pin 35 of the microcontroller 41 as shown in FIG. 4 and pin 2 of the relay RELAY5 as shown in FIG. 9. The output of switch SW-5 is provided at pin 3 of the relay RELAY5 to produce an output signal that is supplied as a working signal in a low current or low power mode of operation to the counter electrode contact CNT for the counter electrode at the receptacle 35 as shown in FIGS. 1 and 3. Accordingly, the microcontroller 41 may function to control switch SW-5 so that when relay RELAY5 is activated the low power amp 82 is connected with the counter electrode contact CNT whereas when the controller opens relay RELAY5 over the RLY5 line the low power amp LP OPA 82 is disconnected from the counter electrode contact CNT.

Figure 8:
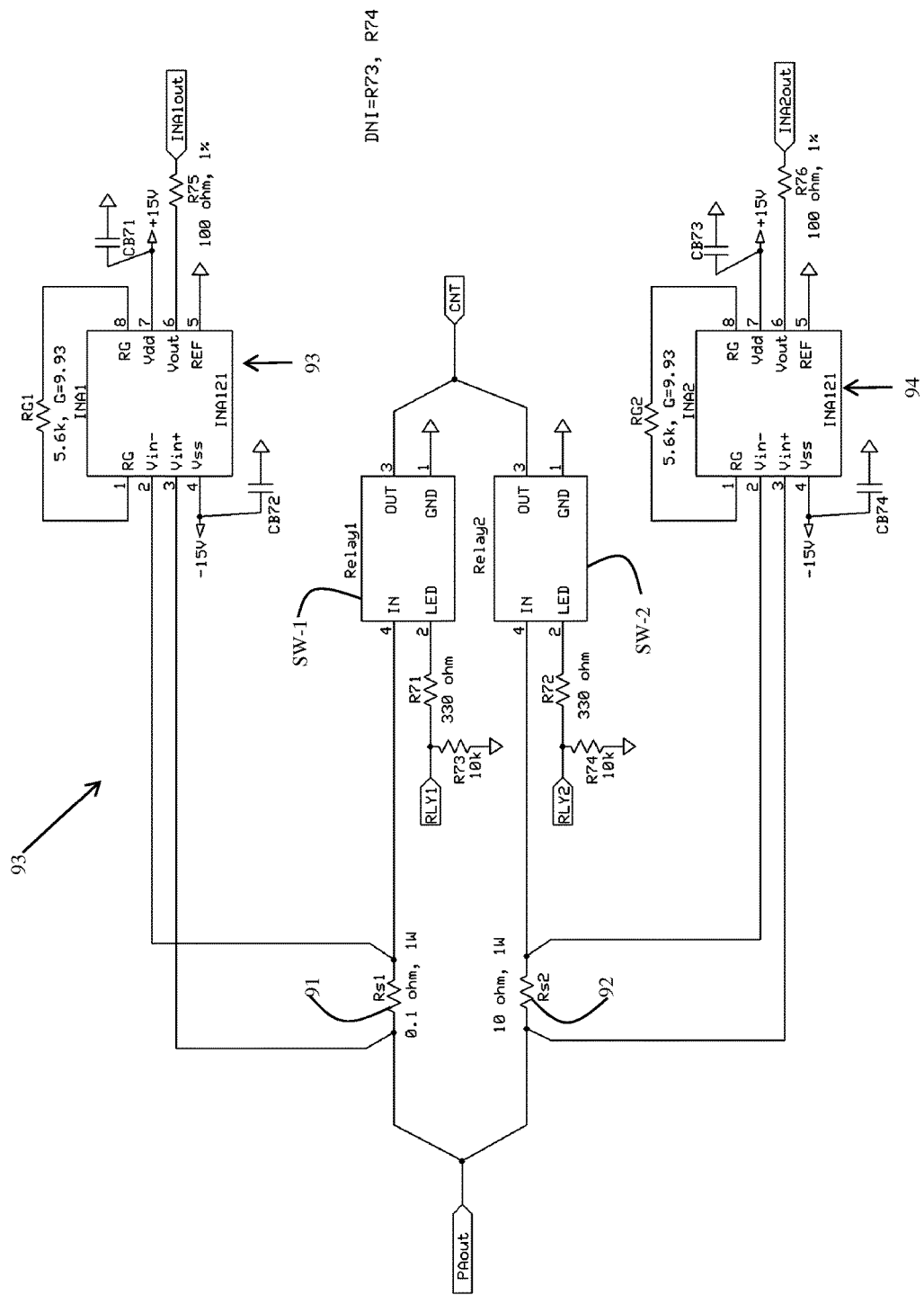
FIG. 8 is a circuit diagram of the high current monitor shown in FIG. 1 and as shown more specifically shown by sense resistors Rs1 and Rs2 and instrumentation amplifiers INA1 and INA2 in FIG. 2.

As shown in FIG. 1, the output from the high current driver 70 is supplied on the PA OUT line to a high current monitor circuit 90 when operating in a high current or high power mode of operation. Referring to FIG. 8, the high current monitor circuitry, generally designated 90, is shown in greater detail along with switches SW-1 and SW-2. As shown in FIG. 8, the high power output signal PAout that is supplied from the high current driver 70 as a working signal is monitored by the high current monitor 90 utilizing a first high current monitoring circuit having a first sense resistor 91 and a first amplifier 93, such as a differential amplifier, preferably in the form of an instrumentation amplifier INA1, as provided by chip INA121. The high current monitoring circuit also includes a second high current monitoring circuit provided by a second sense resistor 92 and a second amplifier 94, such as a differential amplifier, preferably provided by an instrumentation amplifier INA2, as provided specifically by chip INA121 as shown in FIG. 8. As shown, the output on line PAout from the high power amp 72 is supplied through the first sense resistor RS1 91 and through the first switch SW-1 to the counter electrode contact CNT and is also supplied in parallel to the second sense resistor RS2 92 through the second switch SW-2 to the counter electrode contact CNT. The first and second sense resistors are selected to have different resistance so that the first high current monitoring circuit utilizing sense resistor 91 may be employed for a first range of current on line PAout from the high power op amp HP OPA 72 and the second high current monitoring circuit employing sense resistor 92 will be utilized for a second current range on line PAout from the high power op amp HP OPA 72. Switch SW-1 is preferably provided by a digitally controlled analog relay RELAY1 that operates under the control of the microcontroller 41 over relay line RLY1 between pin 30 of the microcontroller 41 as shown in FIG. 4 and pin 2 of the relay circuit RELAY1 as shown in FIG. 8. Likewise, the microcontroller 41 also controls the operation of switch SW-2 preferably provided by a digitally controlled analog relay RELAY2 shown in FIG. 8 over a relay line RLY2 line that connects between pin 31 of the microcontroller 41 a shown in FIG. 4 and pin 2 of the relay circuit RELAY2 as shown in FIG. 8.

For operation in a first range of high current, the high current monitoring circuitry 90 under the control of the microcontroller will operate in such a manner whereby the microcontroller 41 will cause switch SW-1 to close via the relay line RLY1 to connect the output PAout, providing the working current from the high current driver, with the counter electrode contact CNT via sense resistor 91 whereby such current flow is detected by the voltage across the first sense resistor 91. When switch SW-1 is closed by the microcontroller 41, switch SW-2 will be opened under the control of the microcontroller 41 via relay line RLY2. When switch SW-1 is closed the current flowing through the first sense resistor 91 will generate a voltage drop across the first sense resistor 91 proportional to the current flow that will be detected by the differential amplifier 93 that may be in the form of an instrumentation amplifier as shown in FIG. 8. In response to the voltage drop across the first sense resistor 91, the differential amp 93 will produce an output INA1out dependent on the current flow through the first sense resistor 91 that will be supplied as an input to an analog-to-digital converter circuit ADC 110, as shown in FIG. 1, for monitoring by the microcontroller 41. The output from the differential amp 93 at INA1out can also be used as a feedback signal (of INA OUT shown in FIG. 1) for supply to the feedback multiplexer 100 MUX as shown in FIG. 2. Referring again to FIG. 8, when operating in a second high current range the microcontroller 41 will cause switch SW-1 to open by signals over relay line RLY1 and cause switch SW-2 to close by signals over relay line RLY2 so that the second sense resistor 92, having a different resistance than the first sense resistor 91, connects the output of working current PAout from the high current driver with the counter electrode contact CNT through the second switch SW-2. When switch SW-2 is closed the current flow through the second sense resistor 92 will generate a proportional or dependent voltage drop that can be monitored by the differential amplifier 94 provided in the form of an instrumentation amplifier INA2 to detect the voltage drop across the second sense resistor. In response to a voltage difference detected across the second sense resistor 92, the differential amplifier 94 will supply an output signal INA2out dependent on the detected voltage, that can be used as a feedback signal (of INA OUT shown in FIG. 1) to the feedback multiplexer MUX 100 as shown in FIGS. 1 and 2. In addition, the output INA2out supplied from the differential amplifier 94 can also be supplied as an input INA OUT to the ADC circuitry 110 as shown in FIG. 1 for monitoring by the controller 40.

Figure 14:
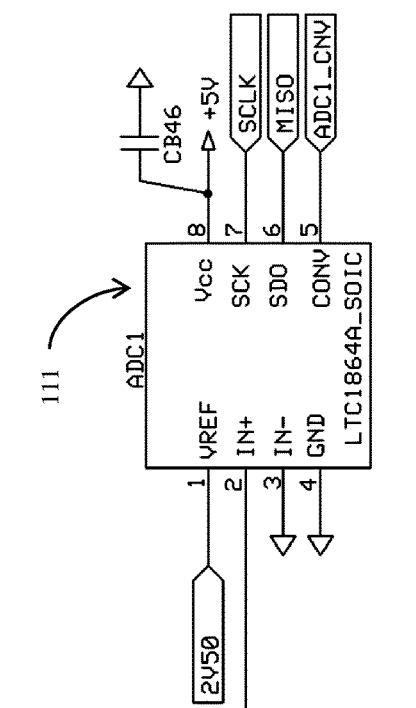
FIG. 14 is a circuit diagram of an analog-to-digital converter circuit ADC-HC1 and associated conditioner circuit as depicted in FIG. 2 and as incorporated into the ADC circuit shown in FIG. 1.

As shown generally in FIG. 2, the output INA-1 OUT from differential amplifier 93 can be supplied for monitoring by the controller 40 through conditioner circuitry 112 which functions to condition the level of the input signal and buffer such input signal for supply to the analog-to-digital converter circuit ADC-HC1 111. As more specifically shown in FIG. 14, the output from the first monitoring circuitry of the high current monitor is supplied as output signal INA1out to the input of a conditioner circuit 112 provided in the form of a buffer SFT-BUF-1, provided by chip AD822, and associated circuitry, that buffers and conditions the input signal INA1out to proper levels for supply to an analog-to-digital converter 111 provided by ADC circuit chip ADC, provided by chip LTC864A_SOIC, and associated circuitry, that functions to convert the analog input from the conditioner circuit 112 to a digital output for supply to the microcontroller 41.

The ADC circuit chip ADC1 is connected with the microcontroller 41 over an interface bus 115, as shown in FIGS. 1 and 2, that includes a clock line SCLK, and a master input/slave output line MISO and a control line ADC1_CNV that respectively connect with pins 58, 57, 56 of the microcontroller 41 as shown in FIG. 4.

Figure 15:
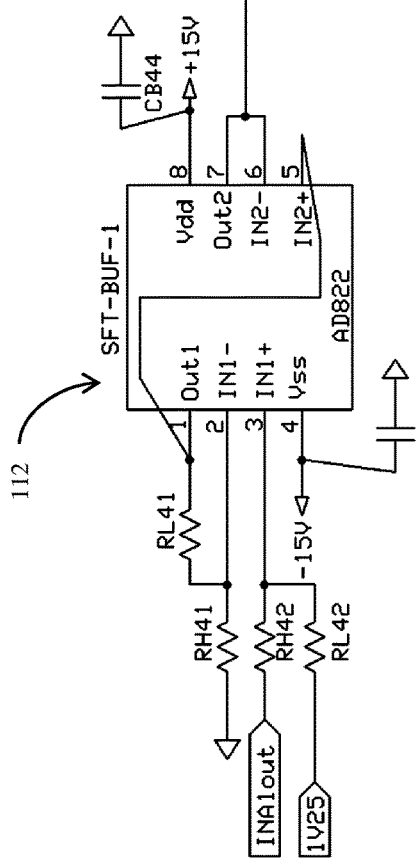
FIG. 15 is a circuit diagram of an analog-to-digital converter circuit ADC-HC2 and associated conditioner circuit as depicted in FIG. 2 and as incorporated into the ADC circuit shown in FIG. 1.

As also generally shown in FIG. 2, the output INA-2 OUT from differential amplifier 94 can be supplied for monitoring by the controller 40 through conditioner circuitry 114 which functions to condition the level of the signal and buffer such signal for supply to the analog-to-digital converter 113. As more specifically shown in FIG. 15, the output from the second monitoring circuitry of the high current monitor is supplied as output signal INA2out to the input of a conditioner circuit 114 which includes a buffer SFT-BUF-2, provided as chip AD822, and associated circuitry, that buffers and conditions the input signal INA2out to proper levels for supply to an analog-to-digital converter 113 provided by ADC chip ADC2, provided by chip LTC1864A_SOIC, and associated circuitry, that functions to convert the analog input from the conditioner circuit 114 to a digital output for supply to the microcontroller 41. The ADC circuit chip ADC2 is connected with the microcontroller 41 over an interface bus 115 as shown in FIGS. 1 and 2. The interface bus 115 includes a clock line SCLK, a master input/slave output line MISO and a control line ADC2_CNV that respectively connect with pins 58, 57, and 55 of the microcontroller 41 as shown in FIG. 4.

The microcontroller 41 is also in electrical communication with the buffer 120 to monitor the voltage at the reference electrode contact REF as generally shown in FIGS. 1, 2 and 3. As shown more specifically in FIG. 11, the buffer 120 includes a buffer chip BUF5, provided as chip AD822, and associated circuitry. The input at pin 3 of the buffer chip BUF5 is connected with the reference electrode contact REF at jack J62 for the reference electrode so that the voltage appearing at the reference electrode contact will be supplied as an input at pin 3 to the buffer chip BUF5. In response, the buffer chip BUF5 supplies an output REFout at output pin 1 through resistor R65. The REFout line from the buffer chip 5 provides a voltage reference feedback signal to the feedback multiplexer MUX 100 as shown in FIGS. 1, 2 and 3 that is buffered for the voltage input at pin 3 from the reference electrode contact REF.

Figure 11:
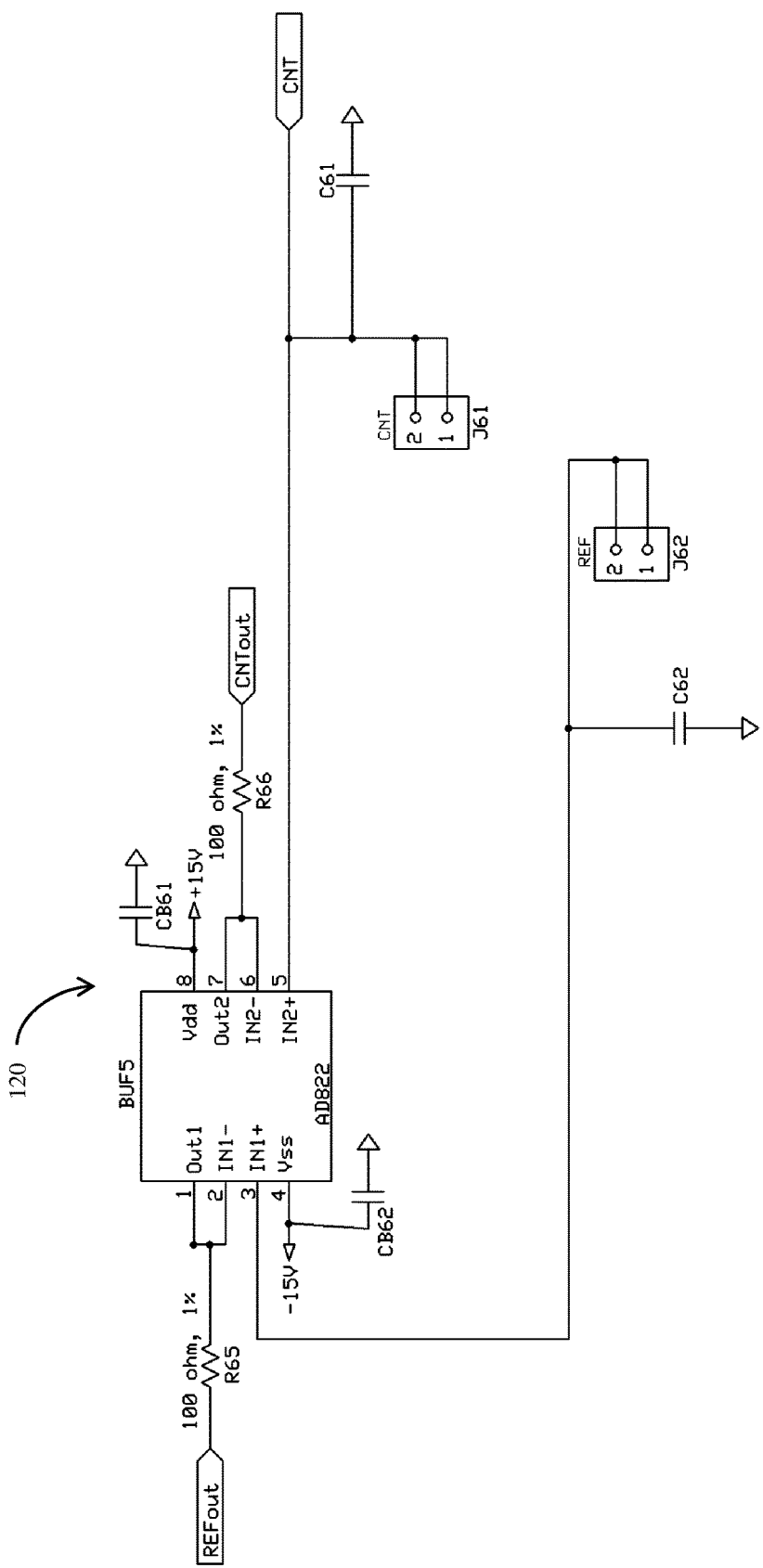
FIG. 11 is a circuit diagram of the buffer circuitry Buffer and the counter electrode contact CNT and the reference electrode contact REF as shown in FIGS. 1-3.
Figure 16:
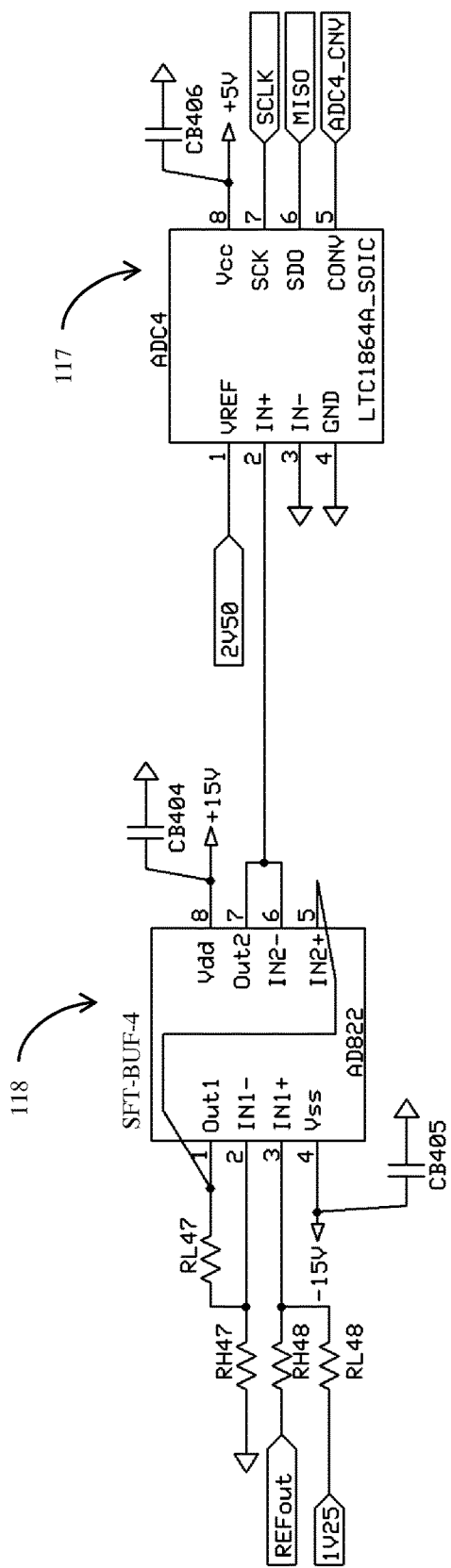
FIG. 16 is a circuit diagram of an analog-to-digital converter circuit ADC-V and associated conditioner circuitry as shown in FIGS. 2 and 3 and as incorporated in the ADC circuit as shown in FIG. 1.

Referring again to FIG. 11, the buffer chip BUF5 connected with the reference electrode contact at jack J62 functions to detect the voltage or signal at the reference electrode contact REF and serves to provide a buffered output REFout at output pin 1 representing the voltage detected at the reference electrode contact REF that can be monitored by the microcontroller 41. For this purpose, the REFout from buffer chip BUF5 is supplied to conditioner circuitry 118, as shown in FIG. 16, that buffers and conditions the signal to an appropriate level to supply to an ADC circuit 117 that converts the analog signal from the conditioner circuitry 118 to a suitable digital signal for supply to the controller 40 over the interface bus 115. As shown more specifically in FIG. 16, the output REFout from the buffer 120, in the form of BUF5 as shown in FIG. 11, is supplied as an input at pin 3 of the buffer chip SFT-BUF-4, as provided by chip AD822, of the conditioner circuit 118. The buffer chip conditions the signal provided as an input at REFout to an appropriate level for input to the ADC circuit 117 provided by ADC chip ADC4 in the form of chip LTC1864A_SOIC. The ADC chip ADC4 communicates with the microcontroller 41 over an interface bus 115 having a clock line SCLK for clocking and timing of signals, a master input/slave output MISO line for transmitting signals to the microcontroller 41 and a control line ADC4_CNV for receiving control signals from the microcontroller 41, respectively connected with pins 58, 57 and 49 of the controller 41, as shown in FIG. 4.

Figure 23:
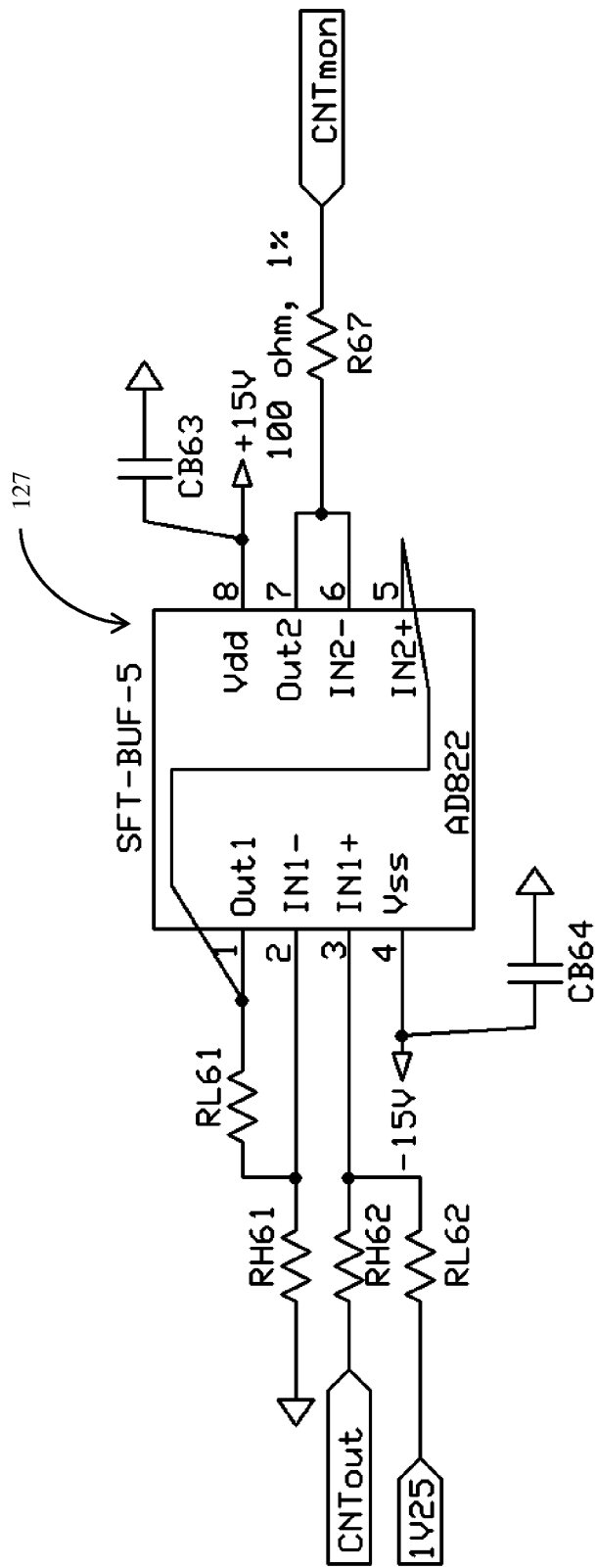
FIG. 23 is a circuit diagram of optional buffer circuitry as incorporated into the buffer of FIG. 1 to enable electrical communication and buffering between the counter electrode contact CNT and the controller MCU as shown in FIG. 1.

Referring back again to FIG. 11, optionally, the buffer chip BUF5 of buffer 120 may also be connected with the counter electrode contact CNT at jack J61 for the counter electrode and selectively with the output line CNT from the high current monitoring circuit 90 selectively through the first and second high current monitoring switches SW-1 and SW-2 as more specifically shown in FIG. 8 or selectively with the output on the output line CNT from the low current driver through switch SW-5 as more specifically shown in FIG. 9. Referring again to FIG. 11, the signal at the counter electrode contact CNT provided by jack J61 is supplied as an input to pin 5 of the buffer chip BUF5. In response, buffer chip BUF5 supplies a buffered output CNTout at pin 7 that can be supplied to ADC circuitry 125 as shown in FIG. 1 for monitoring by the microcontroller 41 over the CNTmon line connected at pin 80 of the controller 41 as shown in FIG. 4. More specifically, with reference to FIG. 23, the CNTout signal from the buffer 120 representing the signal detected at the counter electrode contact CNT can be supplied as an input to a buffer circuit 127 including buffer chip SFT-BUF-5, provided as chip AD822, and associated circuitry, to provide a buffered output CNTmon for supply to the microcontroller 41 and preferably through ADC circuit 125 as shown in FIG. 1.

Figure 10:
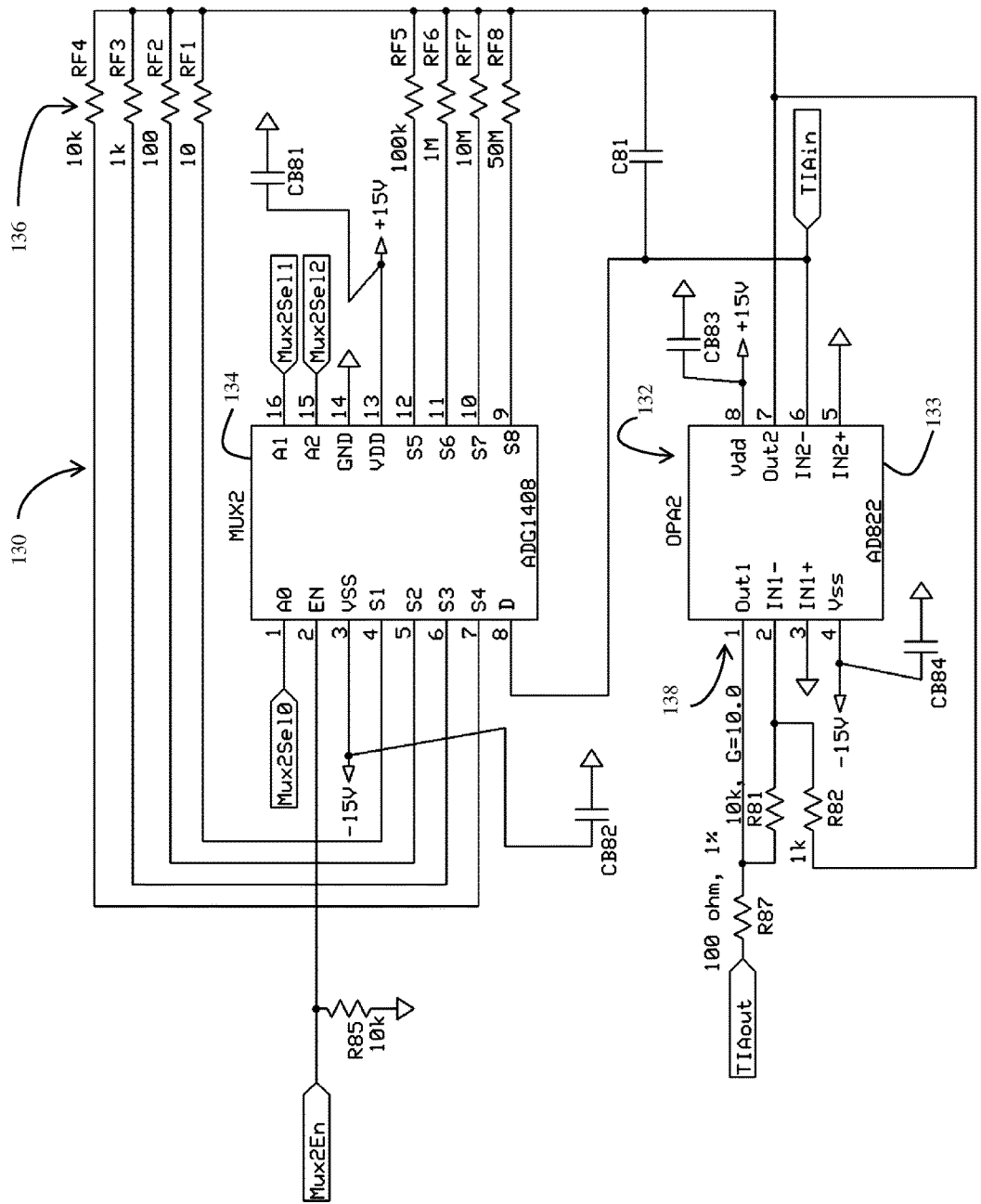
FIG. 10 is a circuit diagram of the low current monitor shown in FIG. 1 and as more specifically shown by the transimpedance amplifier TIA, the −10 gain amplifier and the monitor multiplexer MUX2 and associated resistor array in FIG. 3.
Figure 12:
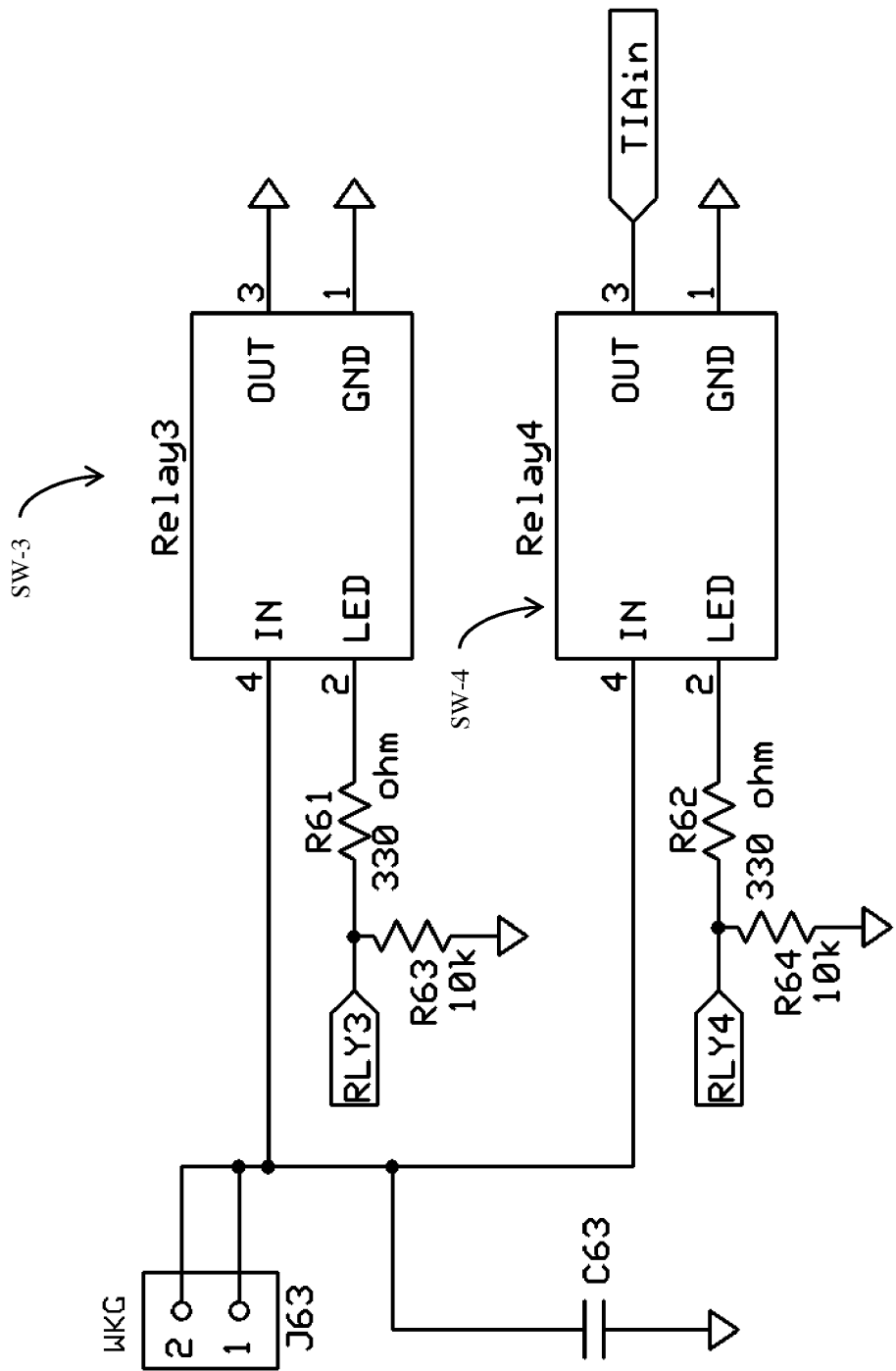
FIG. 12 is a circuit diagram of the working electrode contact WKG and the associated switches SW-3 and SW-4 as shown in FIG. 1 and as shown in greater detail by the working electrode contact WKG and switch SW-3 in FIG. 2 and by the working electrode contact WKG and switch SW-4 in FIG. 3.

As shown in FIG. 1, the working electrode contact WKG may be connected to ground by switch SW-3 when the instrument is configured to operate in the high power or high current mode or alternatively may be connected to the low current monitor 130 by switch SW-4 when the instrument is configured to operate in the low power or low current mode. As shown in greater detail in FIG. 12, the working electrode contact WKG provided at jack J63 is connected as an input to both switches SW-3 and SW-4 at their respective input pin 4. As shown in FIG. 12, switch SW-3 is provided in the form of a relay RELAY3, preferably a digitally controlled analog relay, that operates under the control of the microcontroller over relay line RLY3 that is connected with pin 32 of the microcontroller 41 as shown in FIG. 4. Likewise, switch SW-4 provided in the form of a relay RELAY4, preferably a digitally controlled analog replay, operates under the control of the microcontroller 41 over relay line RLY4 that is connected with pin 33 of the microcontroller 41 as shown in FIG. 4. As such when operating in the high current or high power mode, the microcontroller 41 will cause relay RELAY3 to close thereby connecting the working electrode contact WKG at jack J63 with ground at output pin 3 of the relay RELAY3 and will cause relay RELAY4 to open to cause the working electrode contact WKG provided at jack J63 to be disconnected from the output of relay RELAY4 at the TIAin line at pin 3 of relay RELAY4. When operating in the low power or low current mode, the controller 41 will cause relay RELAY3 to open to disconnect the working electrode contact WKG provided at jack J63 from the ground at output pin 3 and will cause relay RELAY4 to close to connect the working electrode contact WKG with the output line TIAin which in turn connects to the low current monitoring circuitry 130 as shown in FIG. 1. As shown in FIG. 3, when switch SW-4 is closed the TIA in line that is output from switch SW-4 will be supplied as an input to an amplifier provided in the form of an op amp 132 configured as a current follower amplifier or a transimpedance amplifier TIA. The TIA IN line is supplied through switch SW-4 to the inverting terminal of the transimpedance amplifier TIA designated 132. The non-inverting input of the TIA amp 132 is connected to ground as shown in FIG. 3. The output from the TIA amp 132 is supplied both as an input to an amplifier 138 having a gain of negative 10 to invert the signal from the TIA amp for supply as TIAout. In addition, the output from the TIA amp 132 is fed through an array of feedback resistors 136 through a monitor multiplexer MUX 134 under the control of the microcontroller 41 to provide a feedback signal to the inverting input of the TIA amp 132 to thereby provide low current monitoring under the control of the controller 40. The low current monitoring circuitry, generally designated 130, is depicted in greater detail in FIG. 10. With reference to FIG. 10, the signal from the working electrode contact WKG is provided to the monitoring circuitry 130 on the TIAin line through switch SW-4, as shown generally in FIG. 3, and is supplied to the inverting input pin 6 of an op amp circuit OPA2 133, provided by chip AD822, and the associated circuitry, as shown more specifically in FIG. 10. Op Amp OPA2 provides the functionality of the transimpedance amplifier 132 at pins 5-8 and provides the functionality of the negative gain amplifier 138 at pins 1-4. As shown in FIG. 10, the TIAin signal is input at the inverting input pin 6 of Op amp OPA2, while the non-inverting input at pin 5 is connected to ground. The TIA section of op amp OPA2 produces an output at output pin 7 for supply to the resistor array 136, including resistors RF1-RF8, as well as to the input at inverting pin 2 of the negative gain amplifier section of op amp OPA2. The resistor array 136 is connected between the output of the TIA amp 132 at output pin 7 of the TIA amplifier section of op amp OPA2 and the monitor multiplexer MUX2 134, such as a digitally controlled analog multiplexer, as provided by chip ADG1408, which functions to switchably connect a selected resistor in the array under the control of the microcontroller 41 to produce a switchably selected feedback signal that is supplied from output pin 8 of the monitor multiplexer MUX2 to the inverting input at pin 6 of the TIA section of Op Amp OPA2. Considering this feedback loop, from pin 7 of Op amp OPA2, the output of the TIA amp 132 is fed to the resistor array 136 having separate resistors RF4, RF3, RF2, RF1, RF5, RF6, RF7, and RF8, of 10 k, 1 k, 100, 10, 100 k, 1 M, 10 M, 50 M, respectively, connected as inputs to the monitor multiplexer 134 provided as MUX2. The output of the monitor multiplexer 134 is supplied at pin 8 from MUX2 as a feedback input to pin 6 of the op amp OPA2. The multiplexer chip MUX2 communicates with the microcontroller 41 over the MUX2 enablement line MUX2En so the microcontroller 41 can enable and disable the monitor multiplexer MUX2 and over the MUX2 selection lines, Mux2Sel0, Mux2Sel1, Mux2Sel2 lines, so that the microcontroller can switchably select the appropriate resistor in the array 136 for connection in the feedback loop while switchably disconnecting other resistors. The Mux2En line is connected from pin 2 of monitor multiplexer Mux2 to pin 43 of the microcontroller 41 as shown in FIG. 4. Likewise, the Mux2Sel0, Mux2Sel1, Mux2Sel2 lines shown in FIG. 10 are in turn connected with the microcontroller 41 at pins 46, 47 and 48, respectively. The microcontroller 41 functions to send a control signal to enable operation of the monitor MUX2 134 over the Mux2En line. The particular resistor that is selected for connection in the feedback loop is selected by the MUX selection signals sent by the micro processor over the Mux2Sel0-2 lines. The particular resistor of the array 136 that is selected is dependent on the current being monitored on the TIAout line by the microcontroller 41 through conditioner circuit 116 and ADC circuitry ADC-LC 119 as shown in FIG. 3. The TIAout line from the op Amp OPA2 133 also provides a feedback signal from the low current monitoring circuitry to the feedback multiplexer circuitry MUX 100 as shown in FIG. 3 and as shown more specifically in FIG. 6. Referring again back to FIG. 10, the TIAout line from the Amp OPA2 133 is supplied to ADC circuitry 100 as generally shown in FIG. 1 which includes the conditioner circuitry 116 and the ADC circuit ADC-LC 119 as shown in FIG. 3.

Figure 13:
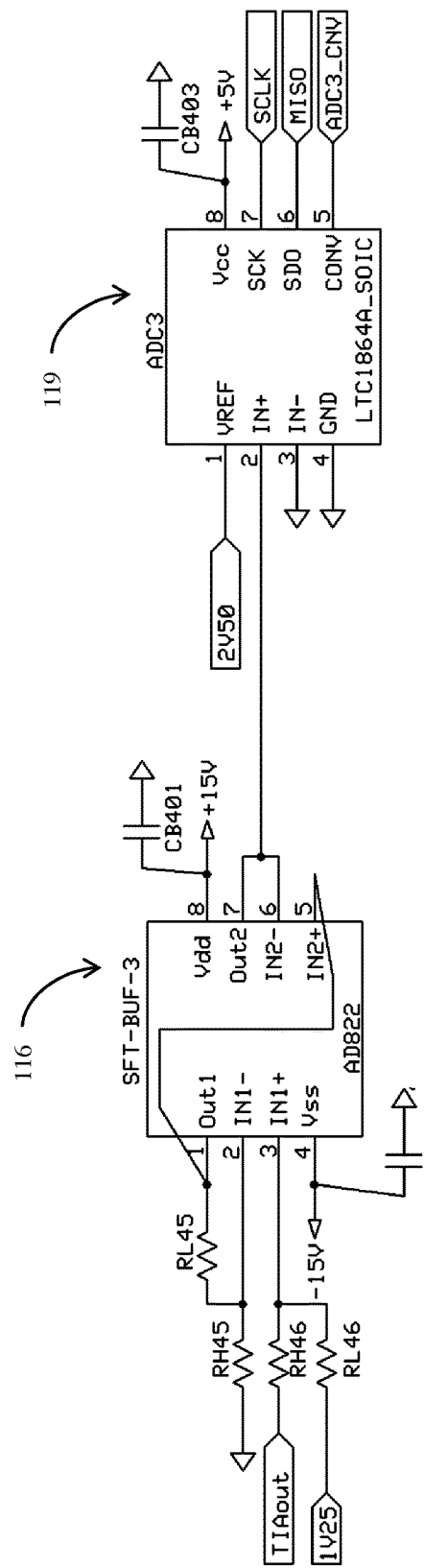
FIG. 13 is circuit diagram of an analog-to-digital converter circuit ADC-LC and associated conditioner circuitry as incorporated in the ADC circuitry shown in FIG. 1 and more specifically as the ADC-LC circuit and conditioner circuitry as shown in FIG. 3.

The conditioner circuitry 116 and the ADC circuitry ADC-LC 119 depicted in FIG. 3 is shown in greater detail in FIG. 13. Referring now to FIG. 13, the conditioner circuitry 116 includes buffer circuitry SFT-BUF-3, as provided by chip AD822, and associated circuitry, which functions to condition and level the analog signal input on the TIAout line to a suitable level for supply to an analog-to-digital converter circuit ADC-LC 119 which is provided by ADC circuit ADC3 in the form of chip LTC1864A_SOIC. The output from the conditioner circuitry 116 at output pin 7 of the buffer SFT-BUF-3 is supplied as an input to pin 2 of the ADC ADC3 circuitry 119 as shown in FIG. 13. As such, the ADC circuitry ADC3 functions to convert the analog signal being supplied to the conditioner circuitry 116 on the TIAout line at pin 3 of the SFT-BUF-3 to a suitable digital signal for monitoring by the microcontroller 41. The ADC circuitry ADC3 119 as shown in FIG. 13 communicates with the microcontroller 41 over an interface bus 115, as shown in FIG. 3, through lines SCLK which provides a clock signal from the microcontroller, the master input/slave output line MISO that provides signals from the ADC circuitry at ADC3 to the microcontroller 41, and the control line ADC3_CNV that provides for control signals from the microcontroller 41 as shown in FIGS. 4 and 13. More specifically, as shown in FIGS. 4 and 13, the clock line SCLK connects pin 7 of the ADC circuit ADC3, as shown in FIG. 13, with pin 58 of the microcontroller 41 as shown in FIG. 4. The MISO line connects pin 6 of the ADC circuit ADC3 as shown in FIG. 13 with the MISO pin 57 of the microcontroller 41 as shown in FIG. 4. Finally, the control line ADC3_CNV connects pin 5 of the ADC circuitry ADC3 as shown in FIG. 13 with pin 50 of the microcontroller 41 as shown in FIG. 3. As such, as generally shown in FIG. 1, the TIA OUT line from the low current monitoring circuitry 130 can be supplied through an ADC circuit 110 so that the analog output from the low current monitor is converted to a suitable digital input signal for supply over the interface bus 115 to the MCU 40 to enable the microcontroller to monitor the signal from the low current monitor.

Figure 6:
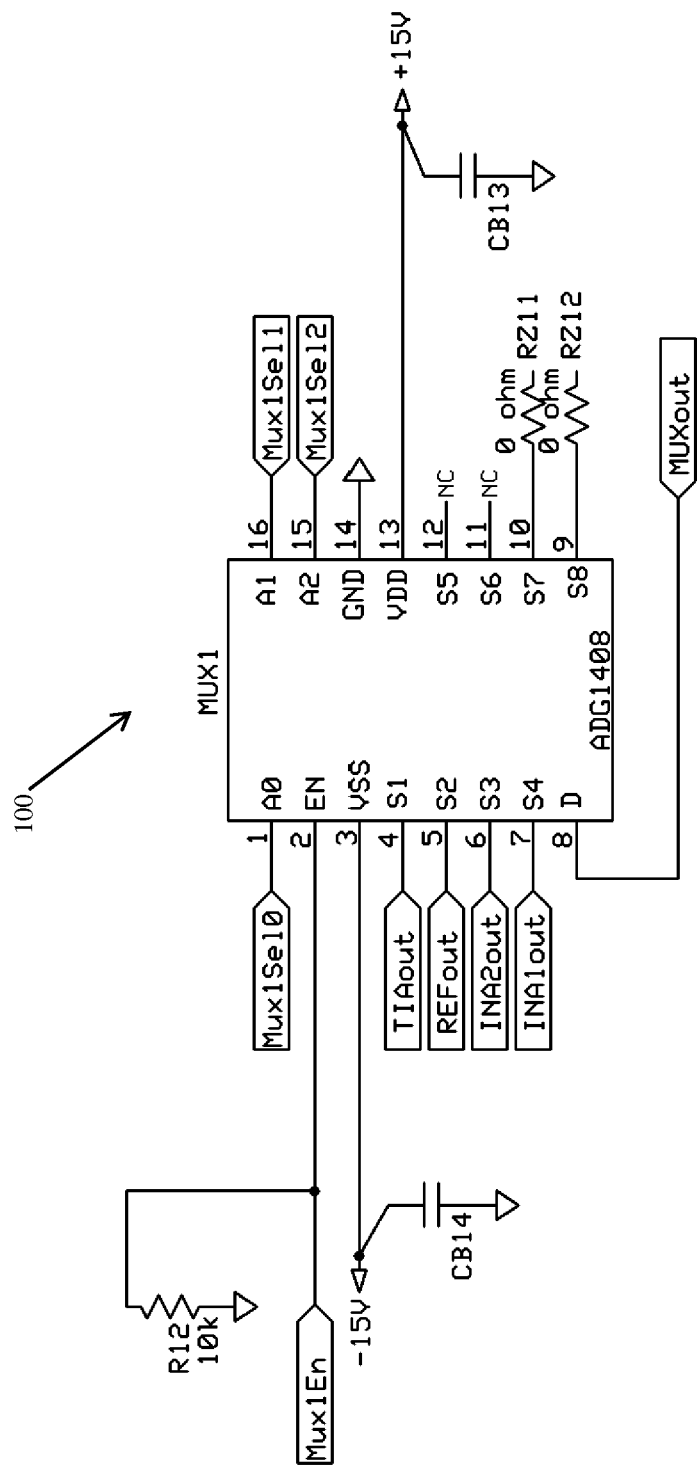
FIG. 6 is a circuit diagram of a feedback multiplexer circuit as shown in general by the MUX in FIGS. 1-3.

As shown in FIG. 1, the MCU 40 is also connected with the feedback multiplexer MUX 100 over an interface bus MUX as shown in greater detail in FIG. 6. The feedback multiplexer 100 may include a multiplexer chip MUX1 in the form of chip ADG1408 and associated circuitry as shown in FIG. 6. The feedback multiplexer MUX1 and associated circuitry functions to provide a digitally controlled analog multiplexer circuit which is connected with the microcontroller 41 as shown in FIG. 4 over the interface bus MUX as shown in FIG. 1. The interface bus MUX includes a multiplexer enablement line MUX1En that connects with pin 63 of the microcontroller 41 shown in FIG. 4 and with pin 2 of the MUX1 circuit as shown in FIG. 6 to provide an enablement line so that the operation of the MUX1 circuit can be enabled by an enablement signal from the microcontroller 41. The interface bus MUX as shown in FIG. 1 also includes the output selection lines MUX1Sel0, MUX1Sel1, MUXSel2, that connect pins 64, 65 and 66, respectively, of the microcontroller 41 as shown in FIG. 4 with pins 1, 16 and 15 of the MUX1 circuit as shown in FIG. 6. The selection lines are utilized so that microcontroller 41 can select which input provided by the feedback signals on the TIAout line connected to pin 4 of MUX1, the REFout line connected to pin 5 of MUX1, the INA2out line connected to pin 6 of MUX1 circuit, and the INA1out line connected to pin 7 of MUX1 may be switchably connected under the control of the microcontroller 41 to provide an output from the MUX1 circuit on the MUXout line connected at pin 8 of the MUX1 chip as shown in FIG. 6. As such, referring to FIG. 1, the MUX1 chip (shown in FIG. 6) of the feedback multiplexer 100 receives as inputs the feedback signal provided on the TIAout line from the low current monitoring circuit 130, the voltage feedback signal provided on the REFout line from the buffer 120 connected with the reference electrode contact REF, the feedback signal supplied on the INA OUT line including the feedback signal on the INA1out line (as shown in FIG. 2) and the feedback signal supplied on INA2out line (as shown in FIG. 2) for different ranges of currents from the high current monitoring circuitry 90. Accordingly, referring once again back to FIG. 6, the microcontroller 41 controls the operation of the feedback multiplexer MUX100 so that the input on the TIAout line is supplied on the MUXout line when operating in low current mode, the input on the INA1out line is supplied on the MUXout line when operating in a high current mode at a first selected range of current, the input on the INA2out line is supplied on the MUXout line when operating in high current mode in a second selected range of current, and the input on the REFout line is supplied on the MUXout line when operating in voltage mode. As shown in FIG. 1, the MUXout line from the feedback multiplexer 100 is supplied as an input to the low current driver 80 and as input to the high current driver 70 so that a feedback signal may supplied to the appropriate driver depending on the mode of operation. More specifically, the MUXout line from pin 8 of the feedback multiplexer MUX100, as shown in FIG. 6, is supplied as an output to the inverting input at pin 2 of the power amp OPA PA 72 as shown in FIG. 7 so that when operating in the high current mode the MUXout signal supplied to the power amp 72 shown in FIG. 7 may selectively be either the feedback signal from line INA-1OUT (as shown in FIG. 2) when operating in the high current mode at a first selected range of current or the feedback signal for line INA-2 OUT (as shown in FIG. 2) when operating in the high current mode at a second selected range of current, or alternatively the feedback signal on the REFOUT line when operating in the voltage mode in the high power or high current operation. The MUXout line, as shown in FIG. 6, is also supplied from pin 8 of MUX1 as an input as shown in FIG. 9 to pin 6 of the low current amp OPA3 82. During operation in a low current or low power mode of operation, the feedback signal on the TIA OUT line (as shown in FIG. 3) from the low current monitor 130 can be supplied as a feedback signal on the MUXout line to the low power amp 82 in low current mode or alternatively the feedback signal or the REFout line can be supplied on the MUX out line to the low power amp 82 when operating in the voltage mode at the low power or low current level.

Figure 24:
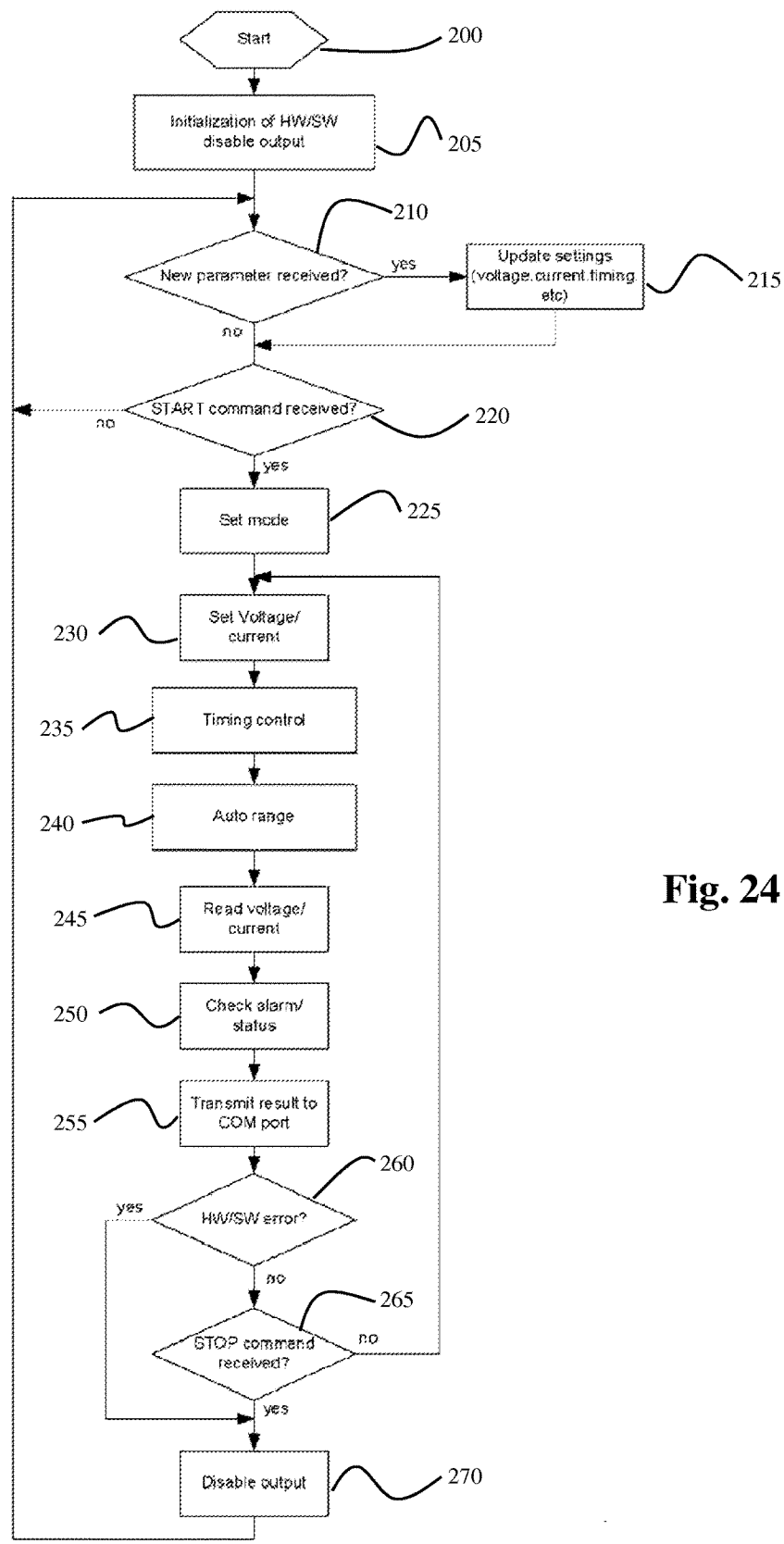
FIG. 24 is a flow chart depicting operational program steps of the instrument having the circuitry generally shown in FIGS. 1-3 and more specifically shown in FIGS. 4-23.

The electrochemical instrument 30 may operate under the control of a computer executed program. An example of a selected program operation is depicted in flow chart form in FIG. 24. Referring to FIG. 24, at start step 200, the electrochemical instrument 30 is initially powered up, or after being powered up is reset, to start operation. At step 205, the hardware and software of the instrument 30 is initialized and the output from the instrument is temporarily disabled. At decision step 210, it is determined whether any new parameters or settings have been received such as current, timing, sequencing or other selected modes of operation. If new settings or parameters have been received, then at step 215 the necessary settings are updated. If no new parameters or settings are received at step 210, or once any such parameters or settings have been updated in step 215, then at step 220 a decision is made to determine whether a START command for starting operation has been received. If not, the program moves back to step 210 to once again determine whether any new parameters or settings have been received. If, however, at decision step 220 it is determined that a START command has been received, the program proceeds to step 225 to set the mode of operation of the instrument 30, such as voltage mode, high current mode or low current mode. At step 230, the instrument will then set the required voltage or current for the selected mode of operation and then at step 235 will set, calculate and control the timing of operation, such as the time for each data point, the total time of the measurement, or other selected timing parameters. Next, the instrument will perform an auto range function at step 240 to detect and automatically select the proper current range by setting the circuitry to achieve the best result such as high resolution, low noise and high dynamic range, for example. At step 245, the instrument will read the reference voltage and output current and then proceed to step 250 to check if there were any warnings or alarms during the measurement. At step 255, the measured result, such as voltage and/or current, may be transmitted to another device such as a host computer or data collector via the communications port. Next, at step 260, the instrument will determine if there were any hardware or software errors detected during the measurement. If so, the program will proceed to step 270 to disable the output. If no errors were detected in step 260 the program will proceed to the decision step 265 to determine whether a STOP command has been received. If a STOP command was been received, the program will again proceed to step 270 to disable the output. If a STOP command is not received at step 265, the program will proceed back to step 230 to again determine the setting of the voltage and current controls to again cycle through the steps from step 230 to step 265. Finally, at step 270, after the output has been disabled, the program will then proceed back to step 210 to determine whether any new parameters or settings have been received and then proceed through the operational steps once again.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

What is claimed is:

1. An electrochemical instrument comprising:
   a. a controller for providing digital control signals;
   b. a digital-to-analog converter (DAC) in electrical communication with the controller for generating an analog output signal in response to digital control signals from the controller;
   c. a high current driver in electrical communication with the DAC to produce a high current range output in response to the analog output signal from the DAC;
   d. a high current monitor in electrical communication with the high current driver, the high current monitor producing a current feedback signal for the high current driver in response to the current monitored by the high current monitor to control the current produced by the high current driver and for supplying an output dependent on the current produced from the high current driver for monitoring by the controller;
   e. a counter electrode contact for electrical communication with a counter electrode and connectable in electrical communication with the output of the high current monitor; and
   f. a working electrode contact for electrical communication with a working electrode connectable in electrical communication with a fixed stable voltage potential for enabling electrochemical analysis of material between the counter electrode and the working electrode, wherein the high current monitor includes a first high current range monitoring circuit for monitoring current in a first current range and a second high current monitoring circuit for monitoring current in a second current range.

2. The instrument of claim 1 wherein the high current monitor includes a first high current range monitoring circuit for monitoring current in a first current range and a second high current monitoring circuit for monitoring current in a second current range and a first high current monitor switch for electrically connecting the first high current range monitoring circuit in and out of electrical communication with the counter electrode contact and a second high current monitoring switch for electrically connecting the second high current monitoring circuit in and out of electrical communication with the counter electrode contact.

3. The instrument of claim 1 including a reference electrode contact for electrical communication with a reference electrode for positioning relative to the working electrode and the counter electrode in communication with the material, and a buffer for electrical communication with the reference electrode contact for detecting voltage at the reference electrode contact and for supplying an output dependent on the voltage at the reference electrode contact buffered from the reference electrode contact for monitoring by the controller and for providing a feedback signal for the high current driver to control the output produced by the high current driver to control the voltage at the reference electrode contact.

4. The instrument of claim 3 including a feedback analog multiplexer in electrical communication with the controller and in electrical communication with the high current monitor for receiving the feedback signal from the high current monitor and the buffer for receiving the feedback signal from the buffer for switchably selecting which of the feedback signals is output by the feedback analog multiplexer for the high current driver under the control of the controller.

5. The instrument of claim 4 wherein the controller controls the feedback analog multiplexer to supply the feedback signal from the high current monitor for the high current driver when operating in high current mode, and to supply the feedback signal from the buffer to the high current driver when operating in voltage mode.

6. The instrument of claim 4 wherein the high current monitor includes a first high current range monitoring circuit for monitoring current in a first current range and a second high current range monitoring circuit for monitoring current in a second current range wherein the first high current range monitoring circuit provides a first high current feedback signal for the feedback analog multiplexer and the second high current range monitoring circuit provides a second high current feedback signal for the feedback analog multiplexer, and wherein the feedback analog multiplexer under control of the controller selectively supplies the first high current feedback signal from the first high current range monitoring circuit for the high current driver when operating in the first high current range and selectively supplies the second high current feedback signal from the second high current range monitoring circuit for the high current driver when operating in the second high current range.

7. The instrument of claim 6 wherein the first high current range monitoring circuit includes a first sense resistor connected in series between the high current driver and the counter electrode contact and a first differential amplifier connected across the first sense resistor to detect the voltage generated by current flow through the first sense resistor to produce the first high current feedback signal, and wherein the second high current range monitoring circuit includes a second sense resistor connected in series between the high current driver and the counter electrode contact and a second differential amplifier connected across the second sense resistor to detect the voltage generated by the current flow through the second sense resistor to produce the second high current feedback signal.

8. The instrument of claim 7 wherein the first and second differential amplifiers include an instrumentation amplifier.

9. The instrument of claim 3 including an analog-to-digital converter (ADC) in electrical communication with the controller and in electrical communication with the outputs of the buffer and the high current monitor to convert the output signals of the buffer and the high current monitor to a digital signal for supply to the controller.

10. The instrument of claim 1 including a high current switch for switchably connecting the high current driver in and out of electrical communication with the counter electrode contact, such that the controller controls the high current switch to switchably connect and disconnect the high current driver in and out of electrical communication with the counter electrode contact.

* * * * *